(12) United States Patent
Bühren et al.

(10) Patent No.: US 9,456,875 B2
(45) Date of Patent: Oct. 4, 2016

(54) DEVICES AND METHODS FOR MONITORING THE ROTATIONAL ORIENTATION OF BONE FRAGMENTS

(75) Inventors: Volker Bühren, Murnau (DE); Ronald Prager, Bovenau (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 501 days.

(21) Appl. No.: 13/996,064

(22) PCT Filed: Dec. 23, 2010

(86) PCT No.: PCT/EP2010/070682
§ 371 (c)(1),
(2), (4) Date: Aug. 8, 2013

(87) PCT Pub. No.: WO2012/084056
PCT Pub. Date: Jun. 28, 2012

(65) Prior Publication Data
US 2013/0317512 A1 Nov. 28, 2013

(51) Int. Cl.
*A61B 17/58* (2006.01)
*A61B 17/60* (2006.01)
*A61F 2/00* (2006.01)
*A61B 19/00* (2006.01)
*A61B 17/17* (2006.01)
*A61B 17/56* (2006.01)

(52) U.S. Cl.
CPC .......... *A61B 19/5244* (2013.01); *A61B 34/20* (2016.02); *A61B 17/1703* (2013.01); *A61B 90/37* (2016.02); *A61B 2017/564* (2013.01); *A61B 2034/2048* (2016.02); *A61B 2090/378* (2016.02); *A61B 2090/3764* (2016.02)

(58) Field of Classification Search
CPC combination set(s) only.
See application file for complete search history.

(56) References Cited

U.S. PATENT DOCUMENTS 6,616,670 B2  9/2003  Simon et al.
7,117,027 B2  10/2006  Zheng et al.
(Continued)

FOREIGN PATENT DOCUMENTS

CN  101574279 A  11/2009
CN  101815477 A  8/2010
(Continued)

OTHER PUBLICATIONS

Inernational Search Report for Application No. PCT/EP2010/070682 dated Sep. 19, 2011.
(Continued)

*Primary Examiner* — Sameh Boles
(74) *Attorney, Agent, or Firm* — Lerner, David, Littenberg, Krumholz & Mentlik, LLP

(57) ABSTRACT

Device and a method for positioning and monitoring the rotary orientation of extremity bone fragments when implanting an intramedullary implant, and in particular to a device and a method for monitoring the rotary orientation of extremity bone fragments of the leg when implanting an intramedullary nail by using a monitoring of locking means of the intramedullary nail which so as to improve the accuracy of the orientation of extremity bone fragments.

9 Claims, 11 Drawing Sheets

(56) References Cited

U.S. PATENT DOCUMENTS

| | | |
|---|---|---|
| 7,686,818 B2 | 3/2010 | Simon et al. |
| 2004/0081341 A1 | 4/2004 | Cherek et al. |
| 2004/0111024 A1* | 6/2004 | Zheng .............. A61B 6/4441 600/426 |
| 2008/0170473 A1 | 7/2008 | Kaiser et al. |
| 2008/0208055 A1* | 8/2008 | Bertram .............. A61B 90/36 600/443 |
| 2012/0197255 A1 | 8/2012 | Elghazaly |
| 2014/0364856 A1 | 12/2014 | Sato |

FOREIGN PATENT DOCUMENTS

| | | |
|---|---|---|
| JP | 2004-130094 A | 4/2004 |
| JP | 2005-500867 | 1/2005 |

OTHER PUBLICATIONS

Hofstetter R et al: "Computer-Assisted Fluoroscopy-Based Reduction of Femoral 29.30 Fractures and Antetorsion Correction". Computer Aided Surgery. Taylor & Francis Inc .• Philadelphia. PA. US. vol. 5. Jan. 1, 2000. pp. 311-325. XP001001432.

* cited by examiner

S10, S20

S30, S32, S36

S40, S50, S52, S56

S60, S62, S63, S64

S10, S20

S30, S32, S36

S40, S50, S52, S56

S10, S20

S30, S32, S36

YY°=+2°
Floor/Horizon

XX°=-100°
Floor/Horizon

+2° to Horizont
ANTT - Display

S40, S50, S52, S56

XX°=+5°
Floor/Horizon

YY°=+17°
Floor/Horizon

+17° to Horizont
ANTT - Display

DEVICES AND METHODS FOR MONITORING THE ROTATIONAL ORIENTATION OF BONE FRAGMENTS

CROSS-REFERENCE TO RELATED APPLICATIONS

The present application is a national phase entry under 35 U.S.C. §371 of International Application No. PCT/EP2010/070682 filed Dec. 23, 2010, published in English, incorporated herein by reference.

FIELD OF THE INVENTION

The present invention relates to devices and methods for monitoring a rotary or rotational orientation of extremity bone fragments when implanting an intramedullary implant, and in particular to a device and a method for monitoring the rotary orientation of extremity bone fragments of the leg when implanting an intramedullary nail.

BACKGROUND OF THE INVENTION

A common therapeutic approach to setting and realigning extremity bone fractures is to implant an intramedullary implant, i.e. a nail for re-establishing or restoring the original position of the extremity bone fragments. Such fractures are generally fractures of the femur or the tibia. A main problem when dealing with the re-establishment of the position of the extremity bone fragments is to find the correct rotary orientation of the extremity bone fragments to avoid substantial damages of the hip or the knee owing to a mal-position of the extremity bone fragments.

A common approach for dealing with the orientation problem is to freehand estimate the correct rotary orientation of the extremity bone fragments with respect to each other. This however leads to substantial deviations of the rotary orientation of the fragments, so that substantial damages of the hip or the knee may occur.

Another approach is to permanently monitor the entire rotary and positional orientation of the extremity bone fragments and the intramedullary nail. This however leads to a high X-ray load and further does not allow for exact positioning of the bone fragments, as the geometry of the anatomy does not allow for exact spatial impression of the position and orientation of the bone fragments.

A femoral neck anteversion guide is for example known from U.S. Pat. No. 5,728,128, according to which a femoral neck anteversion guide is provided for use with a femur having a prepared intramedullary channel, wherein the guide includes a radiolucent stem having a distal end for inserting into the prepared intramedullary channel, and a radio opaque angle locator wire embedded within the stem at a known angle for allowing the femoral neck angle and femoral neck anteversion to be determined. This however also leads to a high X-ray load and further may lead to a non-exact positioning of the extremity bone fragments with respect to their orientation in relation to each other.

SUMMARY OF THE INVENTION

It would be desirable to provide an improved device and method for assisting a surgical incision for implanting an intramedullary nail so as to improve the accuracy of the rotary orientation of extremity bone fragments.

The invention provides a device and method for assisting a surgical incision for implanting an intramedullary nail, a corresponding program element and computer readable medium, according to the subject matter of the independent claims. Further embodiments are incorporated in the dependent claims.

It should be noted that the following described exemplary embodiments of the invention may apply also for the method, the device, the program element and the computer readable medium.

According to an aspect of the invention there is provided a device for assisting a positioning of a first intramedullary bone fragment and a second intramedullary bone fragment of a fractured intramedullary bone to be restored with respect to each other by an intramedullary implant having a proximal end coupled to a targeting device and a distal end, the device comprising a first rotary orientation determining unit for determining a rotary orientation of the intramedullary implant being locked in a predefined orientation to the first intramedullary bone fragment with one of the proximal end and the distal end of the intramedullary implant with respect to an artificial horizon; a second rotary orientation determining unit for determining a rotary orientation of the second intramedullary bone fragment with respect to the artificial horizon; a matching unit for matching the rotary orientation of the intramedullary implant with respect to the rotary orientation of the second intramedullary bone fragment based on the rotary orientation of the intramedullary implant with respect to the artificial horizon and the rotary orientation of the second intramedullary bone fragment with respect to the artificial horizon; wherein at least one of the first rotary orientation determining unit and the second rotary orientation determining units comprise a sensing unit for sensing the actual position of a distal locking means of the intramedullary implant, which sensing allows a positioning of the first intramedullary bone fragment and the second intramedullary bone fragment in the predefined rotary orientation to each other.

The proximal end of a bone is to be understood as the end pointing toward the centre of the human body, wherein the distal end of a bone is to be understood as the end pointing away from the centre of the human body. For example, the hip end of the femur is proximal, whereas the knee end of the femur is distal, and the knee end of the tibia is proximal, whereas the talar end of the tibia is distal. The proximal end of the implant is the end pointing toward a targeting device to which the implant is fixed for handling, wherein the distal end of the implant is the end pointing away from the targeting device. Thus, generally the distal end of the intramedullary implant firstly enters the bone, when being implanted from one of the proximal or distal ends of the bone.

One of the rotary orientation units may be a targeting device, having coupled thereon the intramedullary implant. The targeting device may have a positioning system, based e.g. on a triangulation. Additionally or alternatively the targeting device may have a gravity sensor for determining the rotary orientation with respect to e.g. the floor. One of the rotary orientation units may be an imaging system, which may provide rotary orientation information on a projection direction of an image taken by the imaging device. The imaging device may be an x-ray examination apparatus in form of a C-arm device. It should be noted that the artificial horizon may be eliminated if the device for assisting a positioning of a first intramedullary bone fragment and a second intramedullary bone fragment of a fractured intramedullary bone to be restored with respect to each other (in the following referred to as "device for assisting") directly communicates with the imaging device, i.e. is capable of directly determining the relative position of the imaging system with respect to the position and/or orientation of the targeting device.

According to an exemplary embodiment the device further comprises a reference unit, which may be coupled to an imaging device and being adapted for providing information concerning the rotary orientation of the imaging device with respect to the artificial horizon. As an option, this information may be directly transferred to the device for assisting.

This allows to automatically determine relative positions of different fragments or elements to each other, without the need for the surgeon to manually transfer the orientation data from the imaging device to the device for assisting a positioning of a first intramedullary bone fragment and a second intramedullary bone fragment of a fractured intramedullary bone to be restored with respect to each other. The reference device may for example provide the imaging orientation of an x-ray C-arm device, when being fixedly connected to the C-arm. Such a reference device later on can be supplementary added and calibrated.

According to an exemplary embodiment the reference unit is adapted for providing the orientation of that intramedullary bone fragment, when the imaging device is in an orientation corresponding to a unique imaging projection direction with respect to the corresponding intramedullary bone fragment. A unique imaging projection direction is a projection direction in which an anatomical landmark when imaged shows a characteristic which allows a determination of a clearly defined orientation. Examples thereof will be explained later.

Thus, the reference device may directly provide the rotary orientation information without any further action of the surgeon.

According to an exemplary embodiment the device further comprises an image recognition unit for an image recognition of an image of an anatomical landmark of the intramedullary bone fragment, provided by an imaging device, and an analyzing unit for analyzing the recognized image with respect to an actual imaging projection of an anatomical landmark of the intramedullary bone fragment, taken by the imaging device in relation to an artificial horizon.

Thus, the image recognition may be used to determine the objects imaged and to also determine the spatial orientation and position of these objects. These imaged objects and the corresponding orientations and positions may be analysed so as to give information to surgeon on how to act further, or so as to directly act on devices used by the surgeon. For example, the analysed information may be used to control the imaging device to automatically arrive at a unique imaging projection direction of an anatomical landmark.

According to an exemplary embodiment the device further comprises an actuator for actuating the projection orientation of the imaging device so as to arrive at the unique imaging projection direction of the anatomical landmark of the respective intramedullary bone fragment.

According to an exemplary embodiment the device further comprises an external transmitting unit for transmitting a signal towards an internal transceiving unit, which internal transceiving unit is implantable in a predefined position with respect to a distal locking means of the intramedullary implant, wherein the external transmitting unit being positioned in a predefined position, and an external receiving unit for receiving a signal from the internal transceiving unit being representative for the relative position of the internal transceiving unit with respect to the external transmitting unit.

Thus, the device may directly determine the position of the implant, in particular a distal locking means of the implant, so that this information does not need to be transferred manually be the surgeon. The external transmitting unit and/or the external receiving unit may be implemented in the targeting device. In this case the targeting device functionally belongs to the device for assisting.

According to an exemplary embodiment the device for assisting further comprises the internal transceiving unit, wherein the signal transmission from the external transmitting unit and the internal transceiving unit is conducted wirelessly, and the signal transmission from the internal transceiving unit to the external receiving unit is conducted by acoustic vibrations or acoustic waves.

According to an exemplary embodiment the external transmitting unit is fixedly connected to the targeting device.

According to an exemplary embodiment the external receiving unit is fixedly and acoustically connected to the targeting device.

According to an aspect of the invention there is provided a method for operating a device for assisting of positioning a first intramedullary bone fragment and a second intramedullary bone fragment of a fractured extremity bone to be restored with respect to each other by an intramedullary implant having a proximal end coupled to a targeting device and a distal end, the method comprises determining the orientation of the first intramedullary bone fragment by fitting a first unique imaging projection direction of an anatomical landmark of the first intramedullary bone fragment to the first intramedullary bone fragment; determining a future position of the intramedullary implant in a predefined orientation to the first intramedullary bone fragment; determining a locking position of one of the proximal end and the distal end of the intramedullary implant to the first intramedullary bone fragment; determining a future position of the first intramedullary bone fragment and the second intramedullary bone fragment in a predefined rotary orientation with respect to each other by determining a second unique imaging projection direction of an anatomical landmark of the second intramedullary bone fragment, wherein the orientation of the first unique imaging projection direction and the second unique imaging projection direction to each other corresponds to the predefined rotary orientation of the first intramedullary bone fragment and the second intramedullary bone fragment to each other; determining a locking position of the other of the proximal end and the distal end of the intramedullary implant to the second intramedullary bone fragment; wherein determining a locking position of the distal end of the intramedullary implant to the respective intramedullary bone fragment is conducted by sensing the actual position of a distal locking means of the intramedullary implant, and determining a locking position of the respective intramedullary bone fragment to the intramedullary implant such that the intramedullary implant allows a positioning of the first intramedullary bone fragment and the second intramedullary bone fragment in the predefined rotary orientation to each other.

According to an exemplary embodiment sensing the actual position of a distal locking means of the intramedullary implant comprises using an actual position of a proximal locking means of the intramedullary implant and the orientation of the first unique imaging projection direction and the second unique imaging projection direction are used for providing the surgeon with positional information for the first intramedullary bone fragment and the second intramedullary bone fragment.

According to an exemplary embodiment providing the surgeon with positional information comprises providing displacement information, based on which the surgeon can bring the first intramedullary bone fragment and the second intramedullary bone fragment in the predetermined rotary orientation to each other.

According to an exemplary embodiment sensing the actual position of a distal locking means of the intramedullary implant is conducted by transmitting a signal from an external transmitting unit being positioned in a predefined position, receiving the signal by an internal transceiving unit being fixedly mounted relative to the distal locking means of the intramedullary implant and being actuated by the external transmitting unit, and transmitting by acoustic vibrations or acoustic waves a signal to an external receiving unit as indicative of the relative position of the internal transceiving unit with respect to the external transmitting unit.

According to an aspect of the invention there is provided a method for positioning a first intramedullary bone fragment and a second intramedullary bone fragment of a fractured extremity bone to be restored with respect to each other by an intramedullary implant having a proximal end coupled to a targeting device and a distal end, the method comprises positioning of the intramedullary implant in a predefined rotary orientation to the first intramedullary bone fragment; locking one of the proximal end and the distal end of the intramedullary implant to the first intramedullary bone fragment; determining a rotary orientation of the intramedullary implant with respect to the first intramedullary bone fragment; positioning of the first intramedullary bone fragment and the second intramedullary bone fragment in a predefined rotary orientation with respect to each other by matching the rotary orientation of the intramedullary implant with respect to the second intramedullary bone fragment; locking the other of the proximal end and the distal end of the intramedullary implant to the second intramedullary bone fragment; wherein locking the distal end of the intramedullary implant to the respective intramedullary bone fragment is conducted by sensing the actual position of a distal locking means of the intramedullary implant, and positioning and locking, the respective intramedullary bone fragment to the intramedullary implant such that the intramedullary implant allows a positioning of the first intramedullary bone fragment and the second intramedullary bone fragment in the predefined rotary orientation to each other.

The term "allow" includes a possible future positioning as well as an already established positioning.

It should be noted that the first procedural positioning step, the first procedural locking step and the procedural determining step can be conducted in a varying order. Insofar the positioning and locking is conducted in a tolerable range allowing the subsequent procedural steps, the determining can be conducted afterwards. However, if it is to be expected that the positioning and locking, without the determining step, leads to an intolerant relative positioning of the bone fragment and intramedullary implant to each other, the determining step should be conducted before or during the positioning and locking step.

According to an exemplary embodiment determining a rotary orientation of the intramedullary implant with respect to the first intramedullary bone fragment comprises fitting the first intramedullary bone fragment to a first unique imaging projection direction of an anatomical landmark of the first intramedullary bone fragment, and matching the rotary orientation of the intramedullary implant with respect to the second intramedullary bone fragment comprises fitting the second intramedullary bone fragment to a second unique imaging projection direction of an anatomical landmark of the second intramedullary bone fragment, wherein the rotary orientation of the first unique projection and the second unique projection to each other corresponds to the predefined rotary orientation of the first intramedullary bone fragment and the second intramedullary bone fragment to each other.

According to an exemplary embodiment sensing the actual position of a distal locking means of the intramedullary implant comprises using an actual position of a proximal locking means of the intramedullary implant, and the orientation of the first unique imaging projection direction and the second unique imaging projection direction are used to provide the surgeon with positional information for the first intramedullary bone fragment with respect to the second intramedullary bone fragment.

According to an exemplary embodiment sensing, the actual position of a distal locking means of the intramedullary implant is conducted by transmitting a signal from an external transmitting unit, receiving the signal by an internal transceiving unit being fixedly mounted relative to the distal locking means of the intramedullary implant and being actuated by the external transmitting unit, and transmitting by acoustic vibrations or acoustic waves the received signal to an external receiving unit, as indicative of the relative position of the transceiving unit with respect to the external transmitting unit.

According to an exemplary embodiment the locking direction of an end, of the intramedullary implant corresponds to the respective unique imaging projection direction, of the respective intramedullary bone fragment, to be locked to that respective end of the intramedullary implant.

According to a further aspect of the invention there is provided a method for positioning a proximal femur fragment and a distal femur fragment with respect to each other by an antegrade intramedullary femur nail having a proximal end coupled to a targeting device and a distal end, the method comprising positioning of the antegrade intramedullary femur nail in a predefined orientation to the proximal femur fragment; determining a rotary orientation of the antegrade intramedullary femur nail with respect to the proximal femur fragment by fitting the proximal femur fragment to a first unique imaging projection direction of an anatomical landmark of the proximal femur fragment and sensing the rotary orientation of a proximal locking means of the antegrade intramedullary femur nail with respect to the first unique imaging projection direction; locking the proximal end of the antegrade intramedullary femur nail to proximal femur fragment; positioning of the proximal femur fragment and the distal femur fragment in a predefined rotary orientation with respect to each other by matching the rotary orientation of the antegrade intramedullary femur nail with respect to the distal femur fragment by sensing the rotary orientation of a distal locking means of the antegrade intramedullary femur nail, and by fitting the distal femur fragment to a second unique imaging projection direction of an anatomical landmark of the distal femur fragment with respect to the rotary orientation of the distal locking means; locking the distal end of the antegrade intramedullary femur nail to the distal femur fragment such that the proximal femur fragment and the distal femur fragment are positioned in the predefined rotary orientation to each other.

Thus, it can be guaranteed that the orientation of the first unique imaging projection direction and the second unique imaging projection direction to each other corresponds to the predefined rotary orientation of the proximal femur fragment and distal femur fragment to each other.

According to an exemplary embodiment locking the distal end of the antegrade intramedullary femur nail to the distal femur fragment is conducted by sensing the position of the distal locking means of the antegrade intramedullary femur nail, and positioning and locking the distal femur fragment to the antegrade intramedullary femur nail.

According to a further aspect of the invention there is provided a method for positioning a proximal femur fragment and a distal femur fragment with respect to each other by an antegrade intramedullary femur nail having a proximal end coupled to a targeting device and a distal end, the method comprises positioning of the antegrade intramedullary femur nail in a predefined orientation to the distal femur fragment; determining a rotary orientation of the antegrade intramedullary femur nail with respect to the distal femur fragment by fitting the distal femur fragment to a first unique imaging projection direction of an anatomical landmark of the distal femur fragment and sensing the rotary orientation of a distal locking means of the antegrade intramedullary femur nail with respect to the first unique imaging projection direction; locking the distal end of the antegrade intramedullary femur nail to the distal femur fragment; positioning of the proximal femur fragment and the distal femur fragment in a predefined rotary orientation with respect to each other by matching the rotary orientation of the antegrade intramedullary femur nail with respect to the proximal femur fragment by sensing the rotary orientation of a proximal locking means of the antegrade intramedullary femur nail, and by fitting the proximal femur fragment to a second unique imaging projection direction of an anatomical landmark of the proximal femur fragment with respect to the rotary orientation of the proximal locking means; locking the proximal end of the antegrade intramedullary femur nail to the proximal femur fragment such that the proximal femur fragment and the distal femur fragment are positioned in the predefined rotary orientation to each other.

Thus, it can be guaranteed that the orientation of the first unique imaging projection direction and the second unique imaging projection direction to each other corresponds to the predefined rotary orientation of the proximal femur fragment and distal femur fragment to each other.

According to an exemplary embodiment locking the proximal end of the antegrade intramedullary femur nail to the proximal femur fragment is conducted by sensing the position of the proximal locking means of the antegrade intramedullary femur nail, and positioning and locking the proximal femur fragment to the antegrade intramedullary femur nail.

According to a further aspect of the invention there is provided a method for positioning a proximal femur fragment and a distal femur fragment with respect to each other by an retrograde intramedullary femur nail having a proximal end coupled to a targeting device and a distal end, the method comprises positioning of the retrograde intramedullary femur nail in a predefined orientation to the distal femur fragment; determining a rotary orientation of the retrograde intramedullary femur nail with respect to the distal femur fragment by fitting the distal femur fragment to a first unique imaging projection direction of an anatomical landmark of the distal femur fragment and sensing the rotary orientation of a proximal locking means of the retrograde intramedullary femur nail with respect to the first unique imaging projection direction; locking the proximal end of the retrograde intramedullary femur nail to distal femur fragment; positioning of the proximal femur fragment and the distal femur fragment in a predefined rotary orientation with respect to each other by matching the rotary orientation of the retrograde intramedullary femur nail with respect to the proximal femur fragment by sensing the rotary orientation of a distal locking means of the retrograde intramedullary femur nail, and by fitting the proximal femur fragment to a second unique imaging projection direction of an anatomical landmark of the proximal femur fragment with respect to the rotary orientation of the distal locking means; locking the distal end of the retrograde intramedullary femur nail to the proximal femur fragment such that the proximal femur fragment and the distal femur fragment are positioned in the predefined rotary orientation to each other.

Thus, it can be guaranteed that the orientation of the first unique imaging projection direction and the second unique imaging projection direction to each other corresponds to the predefined rotary orientation of the proximal femur fragment and distal femur fragment to each other.

According to an exemplary embodiment locking the distal end of the retrograde intramedullary femur nail to the proximal femur fragment is conducted by sensing the position of the distal locking means of the retrograde intramedullary femur nail, and positioning and locking the proximal femur fragment to the retrograde intramedullary femur nail.

According to a further aspect of the invention there is provided a method for positioning a proximal tibia fragment and a distal tibia fragment with respect to each other by an antegrade intramedullary tibia nail having a proximal end coupled to a targeting device and a distal end, the method comprising positioning of the antegrade intramedullary tibia nail in a predefined orientation to the distal tibia fragment; determining a rotary orientation of the antegrade intramedullary tibia nail with respect to the distal tibia fragment by fitting the distal tibia fragment to a first unique imaging projection direction of an anatomical landmark of the distal tibia fragment and sensing the rotary orientation of a distal locking means of the antegrade intramedullary tibia nail with respect to the first unique imaging projection direction; locking the distal end of the antegrade intramedullary tibia nail to the distal tibia fragment; positioning of the proximal tibia fragment and the distal tibia fragment in a predefined rotary orientation with respect to each other by matching the rotary orientation of the antegrade intramedullary tibia nail with respect to the proximal tibia fragment by sensing the rotary orientation of a proximal locking means of the antegrade intramedullary tibia nail, and by fitting the proximal tibia fragment to a second unique imaging projection direction of an anatomical landmark of the proximal tibia fragment with respect to the rotary orientation of the proximal locking means; locking the proximal end of the antegrade intramedullary tibia nail to the proximal tibia fragment such that the proximal tibia fragment and the distal tibia fragment are positioned in the predefined rotary orientation to each other.

Thus, it can be guaranteed that the orientation of the first unique imaging projection direction and the second unique imaging projection direction to each other corresponds to the predefined rotary orientation of the proximal tibia fragment and distal tibia fragment to each other.

According to an exemplary embodiment locking the proximal end of the antegrade intramedullary tibia nail to the proximal tibia fragment is conducted by sensing the position of the proximal locking means of the antegrade intramedullary tibia nail, and positioning and locking the proximal tibia fragment to the antegrade intramedullary tibia nail.

According to a further aspect of the invention there is provided a method for positioning a proximal tibia fragment and a distal tibia fragment with respect to each other by an antegrade intramedullary tibia nail having a proximal end coupled to a targeting device and a distal end, the method comprising positioning of the antegrade intramedullary tibia nail in a predefined orientation to the proximal tibia fragment; determining a rotary orientation of the antegrade intramedullary tibia nail with respect to the proximal tibia fragment by fitting the proximal tibia fragment to a first unique imaging projection direction of an anatomical landmark of the proximal tibia fragment and sensing the rotary orientation of a proximal locking means of the antegrade intramedullary tibia nail with respect to the first unique imaging projection direction; locking the proximal end of the antegrade intramedullary tibia nail to proximal tibia fragment; positioning of the proximal tibia fragment and the distal tibia fragment in a predefined rotary orientation with respect to each other by matching the rotary orientation of the antegrade intramedullary tibia nail with respect to the distal tibia fragment by sensing the rotary orientation of a distal locking means of the antegrade intramedullary tibia nail, and by fitting the distal tibia fragment to a second unique imaging projection direction of an anatomical landmark of the distal tibia fragment with respect to the rotary orientation of the distal locking means; locking the distal end of the antegrade intramedullary tibia nail to the distal tibia fragment such that the proximal tibia fragment and the distal tibia fragment are positioned in the predefined rotary orientation to each other.

Thus, it can be guaranteed that the orientation of the first unique imaging projection direction and the second unique imaging projection direction to each other corresponds to the predefined rotary orientation of the proximal tibia fragment and distal tibia fragment to each other.

According to an exemplary embodiment locking the distal end of the antegrade intramedullary tibia nail to the distal tibia fragment is conducted by sensing the position of the distal locking means of the antegrade intramedullary tibia nail, and positioning and locking the distal tibia fragment to the antegrade intramedullary tibia nail.

It may be seen as a gist of the present invention to improve the result when restoring an orientation of bone fragments by using a unique projection of characterizing anatomical landmarks and by using a known orientation of implant landmarks as an inertial reference.

It should be noted that the above features may also be combined. The combination of the above features may also lead to synergetic effects, even if not explicitly described in detail.

These and other aspects of the present invention will become apparent from and elucidated with reference to the embodiments described hereinafter.

BRIEF DESCRIPTION OF THE DRAWINGS

Exemplary embodiments of the present invention will be described in the following with reference to the following drawings.

DETAILED DESCRIPTION OF EXEMPLARY EMBODIMENTS

Figure 1:
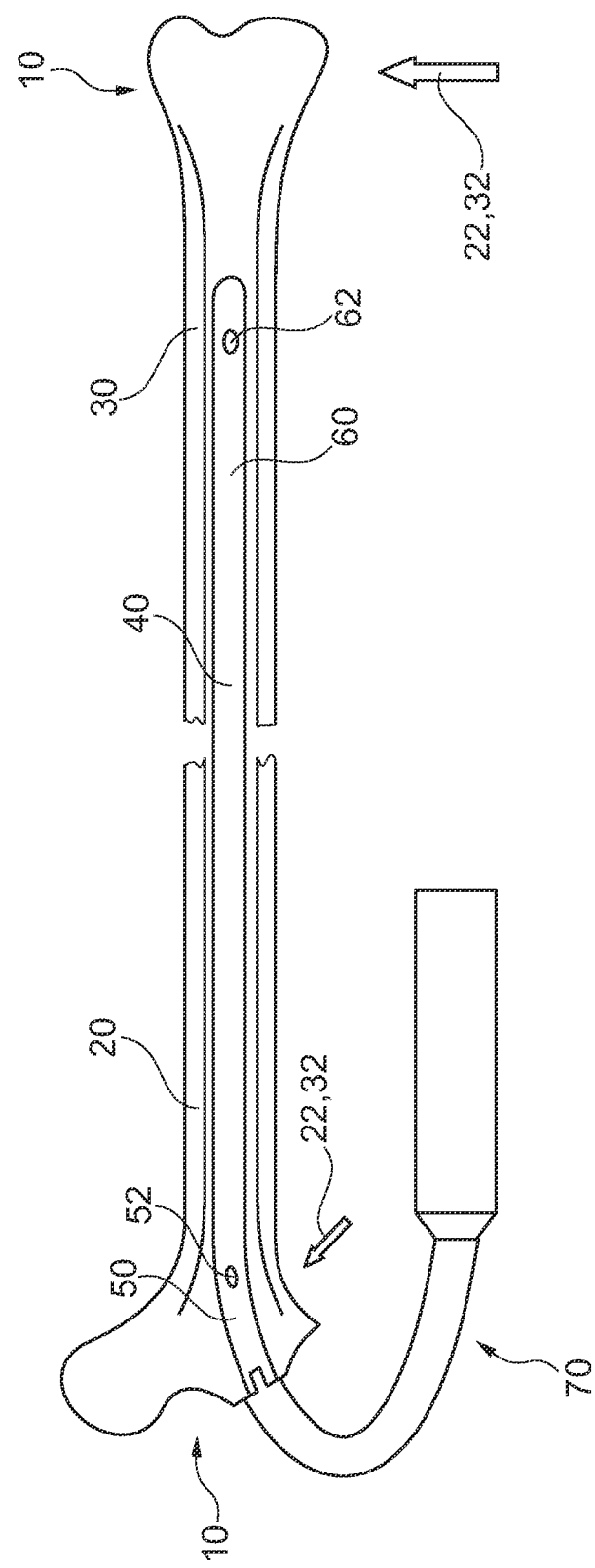
FIG. 1 illustrates an example of a targeting device coupled to an intramedullary implant located internal to a bone fracture.

FIG. 1 illustrates an example of an intramedullary implant and bone fracture and an overview on the position and orientation of an implanted intramedullary implant and extremity bone fragments. The illustration of FIG. 1 relates in particular to a femur bone having implanted therein a femur nail, but may also be transferred to other intramedullary bones like the tibia. FIG. 1 illustrates an antegrade implantation of the femur nail, i.e. to insert the nail from the hip side of the femur. The intramedullary nail may be fixed to a targeting device.

As can be seen from FIG. 1, the extremity bone 10, e.g. the femur, is illustrated in two extremity bone fragments 20, 30. In this embodiment, the first extremity bone fragment 20 is the proximal part of the femur and the second extremity bone fragment 30 is the distal femur fragment. Both fragments are connected by the implanted intramedullary femur nail 40, which femur nail 40 is connected to a targeting device 70 for monitoring and guiding the implantation procedure. The femur nail 40 has a proximal end 50 which proximal end is connected to the targeting device, and a distal end 60, which points away from the targeting device 70. It should be noted that the definition of the proximal end of the intramedullary nail 40 relates to the end which is connected to the targeting device 70, wherein the distal end is defined as the end, pointing away from the targeting device. In the embodiment illustrated in FIG. 1, the proximal end 50 of the intramedullary nail 40 corresponds to the proximal end of the femur 20, wherein the distal end 60 of the intramedullary nail corresponds to the distal femur fragment 30. However, when implanting the femur nail from the knee side of the femur, i.e. retrograde from the distal end of the femur, the targeting device 70 will be in a position proximate to the distal end 30 of the femur bone 10. In this case, which, however, is not illustrated in FIG. 1, the proximal end 50 of the intramedullary nail 40 would correspond to the distal end 30 of the femur 10, and the distal end 60 of the intramedullary nail 40 would correspond to the proximal end 20 of the femur. In other words, the definition of proximal and distal with respect to the bone refers to the position of the bone with respect to the centre of the human body, so that the proximal part of the bone points towards the centre of the human body, wherein the distal part of the bone points away from the centre of the human body. To the contrary, the definition of the proximal end and the distal end of the intramedullary implant refers to the position of the targeting device 70, so that, in particular when applying a retrograde implantation, the definition of proximal and distal of the implant does not correspond to the definition of proximal and distal of the bone.

As can be seen from FIG. 1, the implant comprises a locking device 62 for fixing the implant to the bone fragment. Such locking devices are provided on the distal end 60 of the implant, so that the distal locking means 62 allows a locking of the implant to the distal portion of the femur 30 in the fracture of FIG. 1. Likewise, a proximal locking means 52 is provided at the proximal end 50 of the intramedullary nail 40, allowing a locking of the proximal part of the femur 20.

As a general explanation, particular geometries of the bone are reproducibly known and may be used as anatomical landmarks for an orientation. Such anatomical landmarks are particular unique projections of particular parts of the bone, which are for example the femur neck and femur head, the condyle at the knee or the talar bone. The geometries of an intact extremity bone, in particular the rotary or rotational orientations of the bone ends are known, so that a unique projection of anatomical landmarks can be used to re-establish or restore the position of the bone fragments before any fracture of the bone occurred. For example, the femur at the femur neck has an anteversion of 10-15° over the neutral frontal axis. The sub-talar joint of the tibia for example has an outward rotational shift of 20-25° over the neutral frontal axis. When entirely extending the intact knee joint, the frontal planes are almost identical and rotational movement of the knee joint is not possible.

Thus, according to the clinical practice, at the lower extremity bones, at least three particular imaging device positionings, in particular x-ray device projections, can be conducted under a precise defined rotation: (i) a lateral positioning of the distal femur with a precise projection of the condyles, which corresponds to the frontal plane of the femur and tibia in a full extended knee position, (ii) an anterior-posterior ("AP") positioning of the sub-talar, as well as (iii) a lateral positioning of the sub-talar with a projection of the joint slit without any overlap. For this positioning, the imaging device must be inclined by 20-25° in the AP path of rays and in the lateral path of rays laterally inclined downwardly. The femur condyles can be positioned precise at an AP view so as to arrive at a symmetrical condyle imaging without an overlap of the notch. Likewise, a lateral positioning of the femoral neck can be obtained with a straight imaging of the front edge and a slightly rolling imaging of the back edge, so that a central position of the circular imaging of the femoral head can be obtained. With a reduced precision, the proximal femur can be imaged AP via a half/partial imaging of the trochanter minor, and the proximal tibia via a half/partial imaging of the fibula head.

In particular, when dealing with comminuted fractures, problems can generally be expected at a positioning of the rotary orientation of the femur and the tibia, which result in rotational deviations of more than 10°, thus deviating by more than 10%. The previously described imaging settings or positionings may be used to determine the rotation or rotary orientation of the femur and tibia, respectively. With this respect, the frontal plane of the knee can be defined by a projection of the condyles. Later on, when fixing e.g. a C-arm of the imaging device the hip and talar can be imaged, so that a unique projection of the hip and talar can be used for a positioning of the bone fragments. At the hip joint, the femur head can be seen with a ⅔ circumference of the femur axis. At the tibia, the imaging device can be rotated by 90° into the anterior posterior position, so that the talar can be imaged precisely at 20° outer rotation of the C-arm.

The previously described principle of the rotation monitoring by an imaging device can be simplified and conducted more precisely if one of the main fragments of the bone is fixedly connected to the intramedullary nail in a defined way. If for example the locking close to the knee joint is established exactly in the plane of the condyles, the positioning of the imaging device can be oriented at the second main fragment which is already unlocked, so as to subsequently fix the second main fragment. The positioning of the locking holes at the intramedullary implant can be conducted by a so-called active nail tip targeting ("ANTT") procedure. The ANTT procedure allows precisely determining the position of the nail tip by locating the nail tip. In particular the rotary position of a locking hole at the nail tip can be determined by imaging the locking hole. As the locking hole even if having a thread is almost cylindrical, the projection direction of the imaging device is exactly at the locking direction when the locking hole is exactly circular in the image. However, when the imaging projection direction deviates from the locking direction, the circular locking hole is not circular any longer but e.g. lenticular. It should be noted that ANTT can be used to determine local displacements of the distal locking means owing to bending of the implant, as well as to determine the rotary orientation of the distal locking means and thus of the implant.

The active nail tip technology allows determining the exact rotation of the nail with respect to the bone. With the imaging device, the condyle plane can be exactly determined and both measurements can be technically connected so as to obtain information on the nail rotation over the frontal plane. The targeting device being fixedly connected with the nail is in a defined rotational position allowing the correct joint positioning of the bone by the imaging device. The principle can be used for all intramedullary nails, in particular antegrade or retrograde, proximal or distal locking first.

Figure 2:
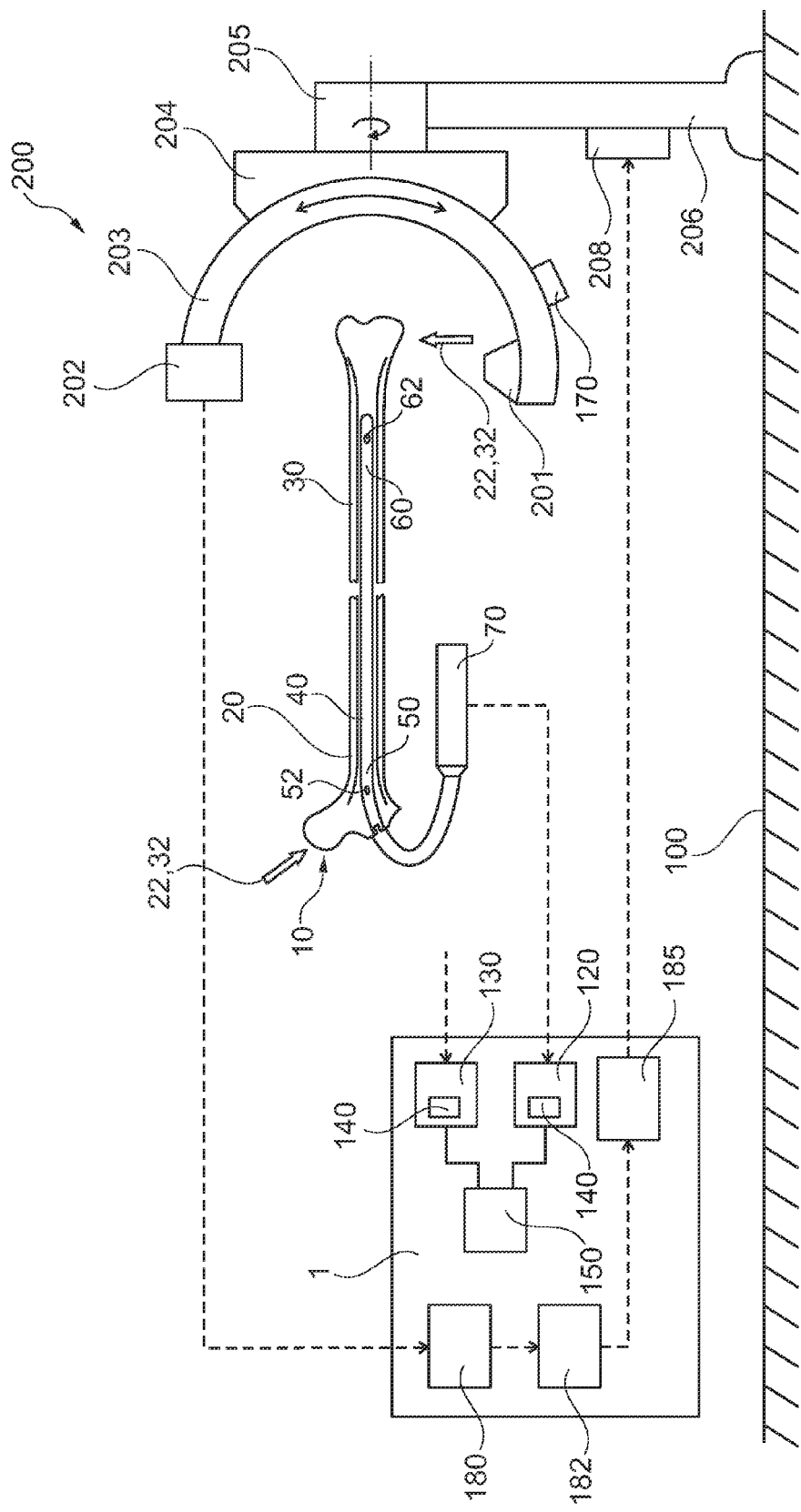
FIG. 2 illustrates a device according to an exemplary embodiment of the invention.

FIG. 2 illustrates a device for assisting the repositioning of bone parts 20, 30 according to an exemplary embodiment of the invention. The device 1 includes a first rotary orientation determining unit 120 and a second rotary orientation determining unit 130. The first rotary orientation determining unit 120 is adapted for determining a rotary orientation of the intramedullary implant being locked in a predefined orientation to the first intramedullary bone fragment with respect to an artificial horizon 100. Thus, it is possible to determine the rotary orientation of the first bone part 20 by a first unique imaging projection direction 22, which can be attained by an imaging device 200. If for example the anatomical geometry of the femoral head is known or can be sufficiently exactly determined by a targeting device, this may also serve as an indicative for a first rotary orientation of the intramedullary implant being locked in a predefined orientation to the first intramedullary bone fragment 20, here the proximal femur fragment 20. The second rotary orientation determining unit 130 serves for determining a rotary orientation of the second intramedullary bone fragment, here the distal femur fragment 30 with respect to an artificial horizon 100 such as the floor of an operating room, for example. Both relative positions, that of the intramedullary implant being locked to the first intramedullary bone fragment as well as the second intramedullary bone fragment can be supplied to a matching unit 150 so as to determine the relative position of the intramedullary implant being locked to the first intramedullary bone fragment with respect to the second intramedullary bone fragment. Thus, the absolute orientation of the respective bone fragment relative to the artificial horizon can be used for determining the relative orientation of the first and second intramedullary bone fragment to each other. Both, the first and the second rotary orientation determining unit 120, 130 comprise a sensing unit 140 for sensing the actual position of a distance locking means of the intramedullary implant so that the first intramedullary bone fragment and the second intramedullary bone fragment can be brought into a predefined rotary orientation to each other. The matching unit 150 can inform the surgeon on a fracture in which the intramedullary bone fragments 20, 30 are in the correct orientation with respect to each other. The matching unit or the device for assisting the surgeon may have a display or any other output device a like voice generator for providing information on the present orientation of the fragments or the required actions to arrive at the predetermined orientation of the fragments with the surgeon.

For determining the correct orientation of the bone fragments, an anatomical landmark like the known geometry of the end portions of a bone can be used, in particular a unique projection, 22, 32 thereof. For this purpose, the imaging device can be brought into an orientation providing the unique projection. When arriving at the position of the imaging device providing the unique projection, the imaging device can provide the orientation of the imaging device relative to the artificial horizon 100, which may be for example the floor of the room. FIG. 2 illustrates the position of the imaging device in the unique imaging projection direction 32 of the condyles of the femur. In this orientation, the x-ray source 201 radiates into the direction of the X-ray sensitive array 202, which illustrates the unique projection in the precise defined orientation, for example of the matching and overlapping condyles. To arrive at the orientation of the unique imaging projection direction, the imaging device 200 can be moved along a circular trajectory with the C-arm 203 over a base 204. Further degrees of freedom can be established by further pivoted connections, e.g. between a base 204 and a bearing 205 connected to a fixed pole 206 having a defined position with respect to the artificial horizon 100. The orientation of the projection direction of the x-ray source 201 can be monitored by a reference device 170 which for example may be capable of determining the spatial orientation of the x-ray source 201 fixedly connected with respect to the orientation of the reference device or reference unit 170. The imaging device 200 may provide the imaging information to an image recognition unit 180 which may be provided in device 1. The image recognition unit 180 may conduct an image recognition of the obtained image of the obtained images so that a connected analyzing unit 182 may conduct an image analyzing so as to provide the surgeon with the information whether the imaging device 200 has arrived at the unique imaging projection direction 32. Further, the analyzing unit 182 can calculate a linear or rotational shift of the x-ray source 201 which is necessary to arrive at the unique imaging direction 32, and can provide this information to an actuator 184. This actuator may provide respective controlling information to the imaging device, which may be adapted to automatically shift the C-arm 203 into the correct position of the correct unique imaging projection direction. The transmission of information can be conducted wirelessly or by a signal line. For this purpose, the imaging device 200 can be provided with a receiving and controlling unit 208 to conduct the automatic repositioning of the C-arm 203 and the x-ray source 201 and the x-ray sensitive array 202. Thus, without a further required action of the surgeon, the device 1 can provide information whether the orientation of the extremity bone fragments 20, 30 are in the predefined orientation with respect to each other and which particular additional rotation has to be conducted by the surgeon to arrive at the correct positioning. The device 1 for assisting the surgeon may have a display or any other output device a like voice generator for providing information on the present orientation of the fragments or the required actions to arrive at the predetermined orientation of the fragments with the surgeon. In particular, when the first extremity bone part 20 is fixedly connected to the intramedullary implant 40 and the intramedullary implant 40 is fixedly connected to the targeting device, the targeting device 70 may provide the rotary orientation of the first intramedullary bone fragment 20 to the device 1, whereas the imaging device 200 when automatically arriving at the unique imaging direction projection provides the respective rotary orientation of the second intramedullary bone fragment 30 to the device, so that the device 1 can directly provide the surgeon on the success of the rotary orientation of the extremity bone fragments 20, 30. When arriving at the predefined orientation of the extremity bone fragments 20, 30, the second fragment 30 can be locked by the locking device 62 to the distal end of the intramedullary nail 40 arriving at a fixedly locked orientation of the first and second intramedullary bone fragment 20, 30 with respect to each other.

Figure 3:
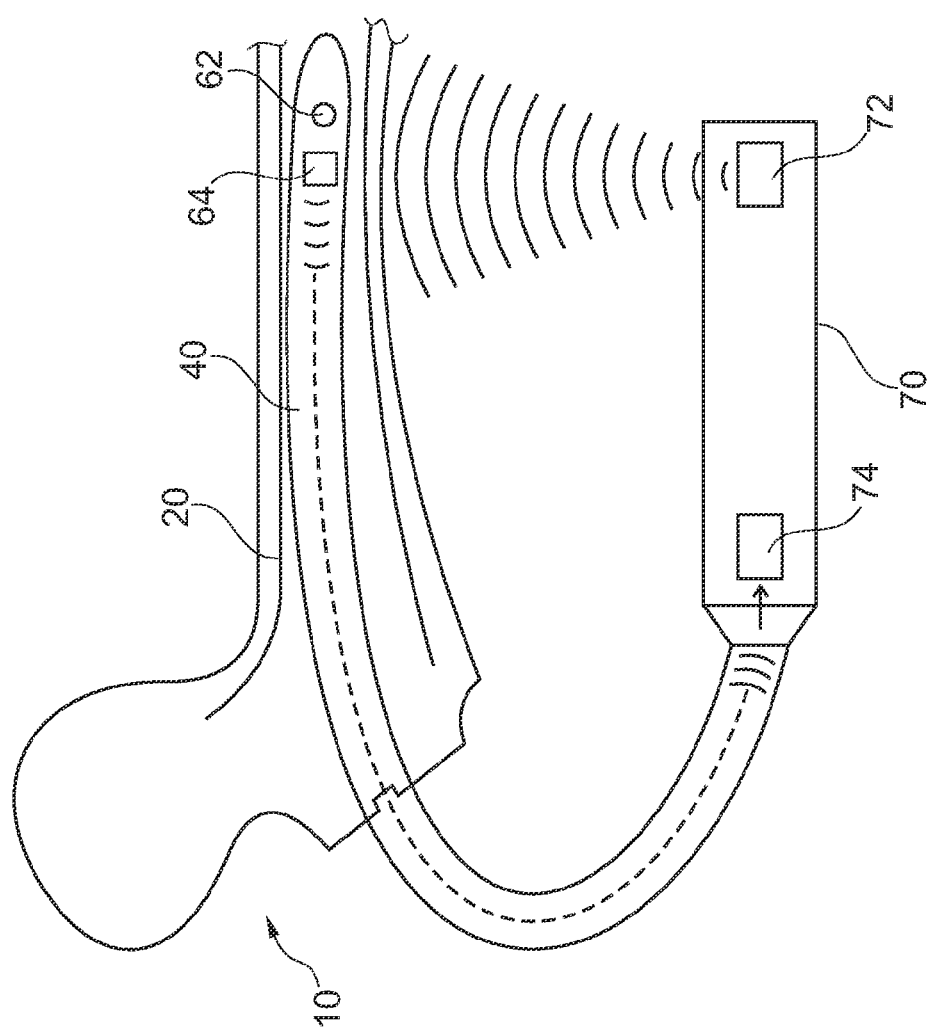
FIG. 3 illustrates a detailed view of the device and intramedullary implant and bone fracture according to an exemplary embodiment of the invention.

FIG. 3 illustrates a detailed view of the device and intramedullary implant and bone fracture according to an exemplary embodiment of the invention, and a schematic overview on the positioning of the distal locking device 62 with respect to the targeting device 70. For this purpose, the targeting device 70 may include an external transmitting unit 72 transmitting a particular signal to an internal transceiving unit 64. The internal transceiving unit together with the external transmitting unit 72 can determine the relative position, so as to arrive at information on the relative position of the internal transceiving unit 64 with respect to the external transmitting unit 72. The internal transceiving unit 64 then transmits this information via the intramedullary nail 40 which may be provided at the targeting device 70. The transmission of the information from the internal transceiving unit to the external receiving unit 74 can be conducted by an acoustic signal transmission via the intramedullary nail 40. Thus, the external receiving unit 74 provides information on the relative position of the internal transceiving unit 64 with respect to the external transmitting unit 72, and when providing the internal transceiving unit 64 close to the locking device 62, also information on the relative position of the locking device 62 with respect to the targeting device 70. This information may be combined with a relative position of the targeting device over an artificial horizon 100, thus leading also to information on the relative position of the distal locking means 62 with respect to the artificial horizon. The artificial horizon may be the floor of the operating room, but may be also any other point serving as a reference point for determining the relative position of the single components with respect to this reference point. For example, the device 1 or a particular vertex of the device 1 may be used as artificial horizon. For determining the orientation of the targeting device or the imaging device over an artificial horizon 100 like the floor of the operation room a gravity sensor may be used. In fact also positioning systems similar to GPS like systems may be used. An operation room may be provided with active or passive reference points serving as triangulation points corresponding to the satellites in a GPS system. The imaging device may also refer to the artificial horizon or the reference point so that the entire system may be used with any imaging system, insofar the imaging system is capable of informing the surgeon on its relative position, e.g. by an optical or electronic inclination scale or positioning system. It should be noted that the artificial horizon 100 may be eliminated if the device 1 directly communicates with the imaging system, i.e. is capable of directly determining the relative position of the imaging system with respect to the internal transceiving unit. The positional information can be provided to the device 1 so as to arrive at the correct positional information on the distal locking device 62. When combining the positional information on the distal locking means 62 obtained by the active nail tip technology as described in FIG. 3 and combining this information with the information obtained by the imaging device 200 by the information on the unique imaging projection direction, this information can be obtained to arrive at the correct predefined position of the first and second intramedullary extremity bone fragment.

Figure 4:
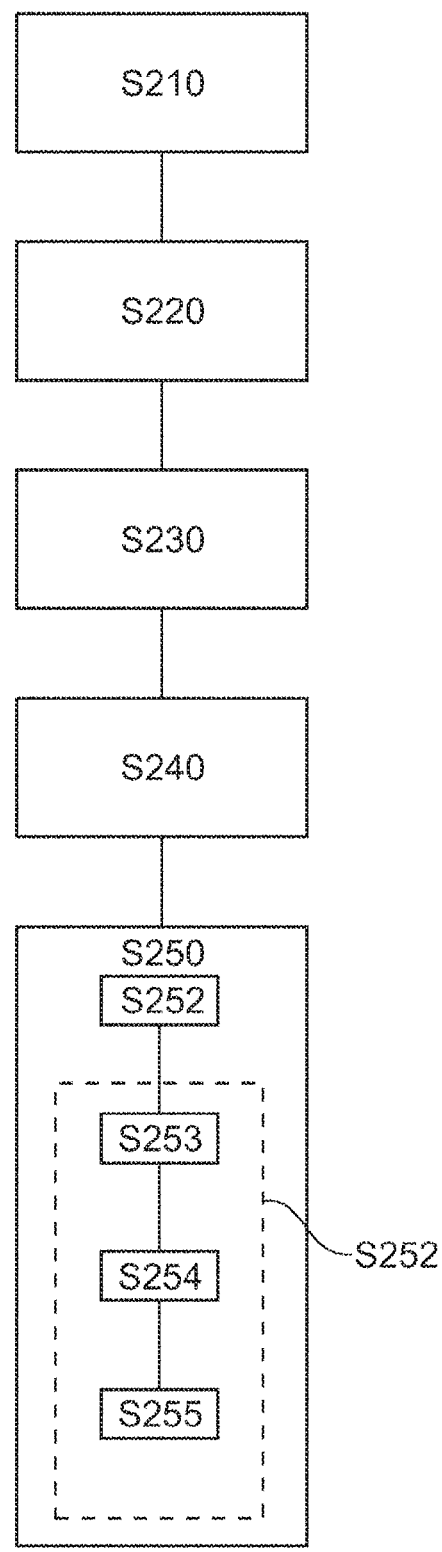
FIG. 4 illustrates a schematic flow of a method for operating the device of FIG. 2 according to an exemplary embodiment of the invention.

FIG. 4 illustrates a schematic flow of a method for operating the device of FIG. 2 according to an exemplary embodiment of the invention. The method for operating the device allow an assisting of positioning a first intramedullary bone fragment 20 and a second intramedullary bone fragment 30 of a fractured extremity bone 10 to be restored with respect to each other by an intramedullary implant 40. The implant has a proximal end 50 coupled to a targeting device 70 and a distal end 60. The device determines S210 the orientation of the first intramedullary bone fragment by fitting a first unique imaging projection direction 22 of an anatomical landmark of the first intramedullary bone fragment to the first intramedullary bone fragment. This first unique imaging projection direction may be for example the femur head and the femur neck being imaged in a projection direction such that the diameter of the neck and the outer circumference of the head are concentric. For the surgeon it is clear that this corresponds to a predefined position. With respect to this position, the device further determines S220 a future position of the intramedullary implant 40, e.g. a femur nail, in a predefined orientation to the first intramedullary bone fragment. The device 1 further determines S230 a locking position of one of that end of the implant, which corresponds to the first bone fragment. This may be the proximal end or the distal end of the intramedullary implant. Now the surgeon may use the position determined by the device to conduct the locking of the first intramedullary bone fragment to the implant. As the orientation of the first bone fragment 20 is known and also the orientation of the implant is known, the implant when locked to the first fragment represents the orientation of the first fragment. Now, an implant landmark like a distal locking means 62 in form of a cylindrical hole may serve as an indicative for the orientation of the first bone fragment 20. It is to be expected that the implant, in particular when being provided as a long intramedullary nail, will bend as to follow the intramedullary channel of the bone. However, the deformation is considered as being limited to the bending, so that not torsion deformation is expected. Thus, even is bending the nail, the rotary orientation of the nail, and at the same time the distal locking hole 62 remains unamended, so that the distal locking hole 62 may serve as a rotary or rotational indicator for the rotary orientation of the first bone fragment 20. It should be noted that the device may firstly determine the locking position S230 and then determine the rotary orientation of the first fragment 20 and the implant 40 in S210 and S220, if the locking position is in a general allowable range. A matter of fact, the order of S210 and S220 can be vice versa, and S230 may be conducted between S210 and S220, and S210, S220 and S230 at least partially may be conducted at the same time or interleaved. The device 1 based on the previous determinations now may determine S240 a future position of the first intramedullary bone fragment and the second intramedullary bone fragment in a predefined rotary orientation with respect to each other. This can be done by determining a second unique imaging projection direction 32 of an anatomical landmark of the second intramedullary bone fragment, and to bring the second unique imaging direction 32 into a relation to the orientation of the distal locking hole 62, which is represents the first unique imaging direction of the first fragment. This information may be used to provide the surgeon with information, on how to amend the current orientation so as to arrive at the optimal predefined orientation of the first unique projection and the second unique projection to each other, thus corresponding to the predefined rotary orientation of the first intramedullary bone fragment and the second intramedullary bone fragment to each other. The device 1 may only inform the surgeon on the subsequent steps, e.g. on how to rotate the second fragment 20 over the implant 40 being locked to the first fragment 10, but may also control the imaging device to move into the position in which the imaging device has the imaging direction which corresponds to the optimal predefined orientation, so that the surgeon only has to rotate the second fragment into a position meeting the second unique imaging projection direction, here the matching contours of the condyles. Determining the locking position of the distal end of the intramedullary implant to the respective intramedullary bone fragment is conducted by sensing S252 the actual position of a distal locking means 62 of the intramedullary implant, and determining S255 a locking position of the respective intramedullary bone fragment to the intramedullary implant such that the intramedullary implant, in particular the predefined geometry of the distal locking means allows a positioning of the first intramedullary bone fragment and the second intramedullary bone fragment in the predefined rotary orientation to each other.

As additional assistance, which is however not mandatory, the device determines a locking position of the other of the proximal end and the distal end of the intramedullary implant to the second intramedullary bone fragment, in FIG. 2 the distal end of the implant to the distal fragment 20. This will be conducted by the procedure as described with respect to FIG. 3. In particular the bending displacement of the nail tip 60 as the distal end of the implant will be determined so that a locking screw may inserted at the predefined position. This avoids an erroneous drilling for the locking procedure at the distal end of the implant. Although this targeting procedure may also be applied to the locking of the proximal end of the implant, the proximal locking means 52 of the implant 40 as a rule is sufficiently exact defined by the targeting device 70. In other words, possible bending deformations at the proximal end do not lead to a substantial deformation, but the distal end does. It should be noted that the locking targeting S250 at the distal end may be left out when no bending is expected or other targeting methods are used. In this case step S250 can be left out without departing the invention.

The sensing S252 of the actual position of a distal locking means 62 of the intramedullary implant 40 may be conducted by transmitting S253 a signal from an external transmitting unit 72 being positioned in a predefined position, e.g. with respect to the targeting device 70. An internal transceiving unit 64 receives S254 the signal. The internal transceiving unit 64 is fixedly mounted relative to the distal locking means 62 of the intramedullary implant 40 and being actuated by the external transmitting unit. The internal transceiving unit 64 provides information on relative position with respect to the external transmitting unit 72 based on the received signal. For this purpose the signal may comprise a combination of different frequencies, phase shifts etc, allowing the internal transceiving unit 64 to determine the relative position with respect to the external transmitting unit 72. The relative position may include linear displacement as well as rotational displacement. Although a relevant elongation of the implant is not expected and also no torsion, the internal transceiving unit may be adapted to determine displacements in all six degrees of freedom. It should be noted that the internal transceiving unit 64 may also transmit a raw data signal and the evaluation thereof may be conducted somewhere else, e.g. in a particular unit (not shown) in the device 1. Although transmitting S255 may be conducted by acoustic vibrations or acoustic waves, the signal may also be transferred as a wireless radio signal, a signal via wire or any other appropriate signal transmission. The signal, as indicative of the relative position of the internal transceiving unit 64 with respect to the external transmitting unit 72, may be transmitted to an external receiving unit 74 being located at the targeting device.

Figure 11:
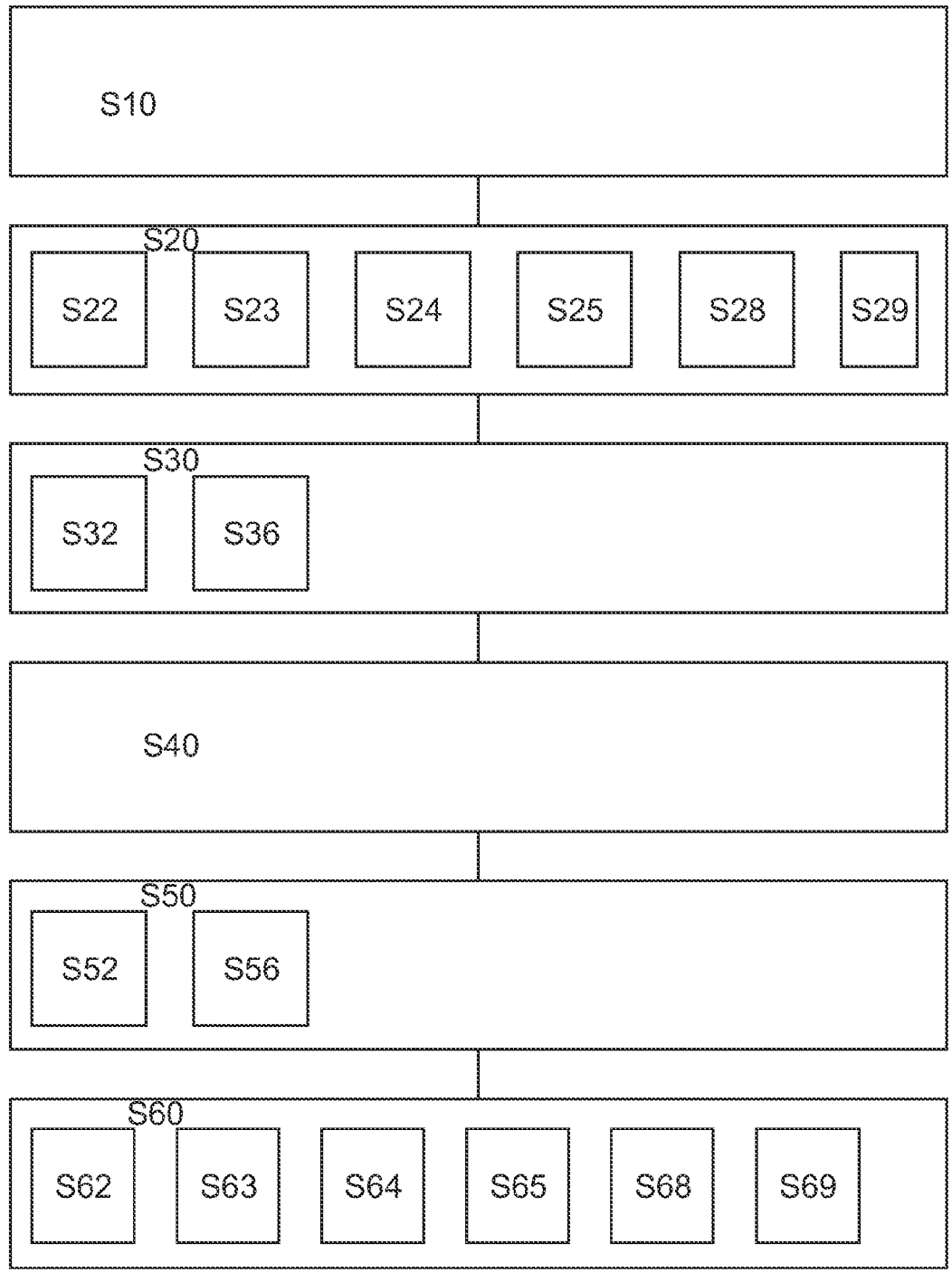
FIG. 11 illustrates a more detailed visualization of the procedural steps of the method for setting the re-establishment of the orientation of extremity bone fragments according to an exemplary embodiment of the invention.

In the following five different operations will be described with respect to FIGS. 5, 6, 7, 8 and 9. The respective steps refer to the step remarks in said figs. and to FIG. 11 illustrating a more detailed visualization of the procedural steps of the method for dealing the re-establishment of the orientation of extremity bone.

Figure 5A:
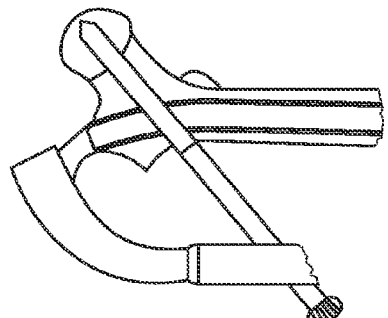
FIGS. 5a-5d illustrate several procedural steps of a method for setting and orienting a femur fracture with an antegrade entry of the intramedullary femur nail with primary proximal locking.
Figure 5A:
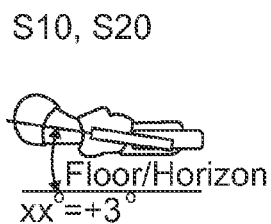

FIGS. 5a-5d illustrate several procedural steps of a method for dealing a femur fracture with an antegrade entry of the intramedullary femur nail with primary proximal locking. The nail will be inserted and the neck screw will be placed in the centre of the neck and the femur head (FIG. 5a). The nail is rotated by 10° to 15° outward in the fragment and can be localized by the method described with respect to FIG. 3. A collimation unit at the imaging device 200 then is rotated by 10° to 15° inwardly, and the distal fragment is rotary positioned while monitored via the imaging device 200, so that the contour of the condyles match, i.e. are in the same plane as the collimation unit. Now the distal locking can be conducted using the method described with respect to FIG. 3.

Figure 5B:
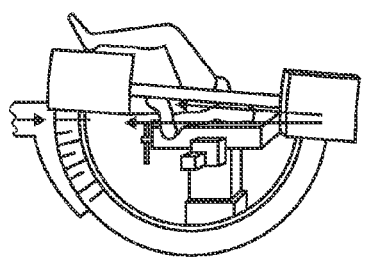
Figure 5C:
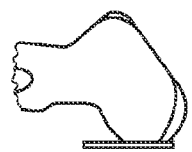
Figure 5C:
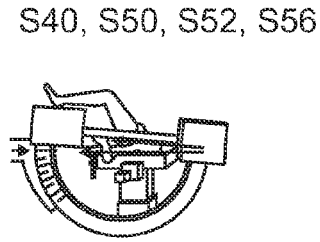
Figure 5C:
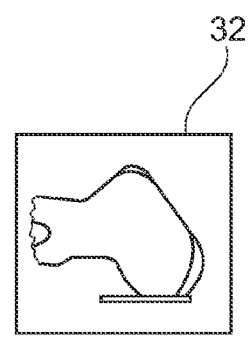
Figure 5D:
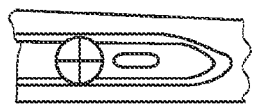
Figure 5D:
Figure 5D:
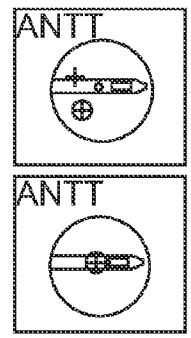

In more detail, the method for positioning a proximal femur fragment 20 and a distal femur fragment 30 with respect to each other by an antegrade intramedullary femur nail 40 having a proximal end 50 coupled to a targeting device 70 and a distal end 60 is conducted by the following steps. As can be seen in FIG. 5a, the antegrade intramedullary femur nail is positioned S10 in a predefined orientation to the proximal femur fragment 20 and a rotary orientation of the antegrade intramedullary femur nail with respect to the proximal femur fragment is determined S30. This can be done by fitting S36 the proximal femur fragment to a first unique imaging projection direction 22 of an anatomical landmark of the proximal femur fragment and sensing S32 the rotary orientation of a proximal locking means 52 of the antegrade intramedullary femur nail with respect to the first unique imaging projection direction. However this step can be left out, if the locking of the proximal end 50 of the femur nail 40 can be conducted otherwise, i.e. free hand by the extended experience of a surgeon, using the targeting device 70. If the correct position of the proximal femur fragment to the femur nail 40 is found, the proximal end of the antegrade intramedullary femur nail is locked S20 to the proximal femur fragment. The implant landmark of the femur nail, e.g. the distal locking hole 62 is used as an indicative for the rotary orientation of the proximal femur fragment. The proximal femur fragment and the distal femur fragment 30 are positioned S40 in a predefined rotary orientation with respect to each other by matching S50 the rotary orientation of the antegrade intramedullary femur nail with respect to the distal femur fragment by sensing S52 the rotary orientation of a distal locking means 62 of the antegrade intramedullary femur nail, and by fitting S56 the distal femur fragment to a second unique imaging projection direction 32 of an anatomical landmark of the distal femur fragment with respect to the rotary orientation of the distal locking means. For this purpose the imaging device, e.g. in form of a C-arm moves to the distal end, i.e. the femur condyles, as can be seen in FIG. 5b, and can be adjusted by the x-ray calculation of the inclination of the femur head of +3°, as can be seen in FIG. 5a, and subtracting 10° (to) 15° antetorsion as described above, resulting in −7° (to) 12° antetorsion, which should be the orientation of the imaging device, e.g. visible on a scale of the imaging device. Subsequently the condyles fragment is rotated to be in line with the orientation of the imaging device 200, resulting in an image of the unique imaging projection direction 32 of the femur condyles, as can be seen in FIG. 5c. Subsequently, the distal locking means 62 of the femur nail will be locked by using the method described with respect to FIG. 3, as can be seen in FIG. 5d. Locking the distal end of the antegrade intramedullary femur nail to the distal femur fragment may be conducted by sensing S62 the position of the distal locking means of the antegrade intramedullary femur nail, and positioning S63 and locking S64 the distal femur fragment to the antegrade intramedullary femur nail. Thus, a locking S60 can be established between the distal end of the antegrade intramedullary femur nail to the distal femur fragment such that the proximal femur fragment and the distal femur fragment are positioned in the predefined rotary orientation to each other.

Figure 6A:
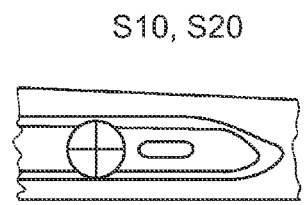
FIGS. 6a-6c illustrate a method for setting and orienting a femur fracture with an antegrade entry of a femur nail with proximal distal locking.
Figure 6A:
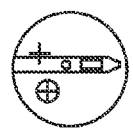
Figure 6A:
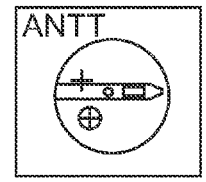
Figure 6A:
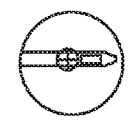
Figure 6A:
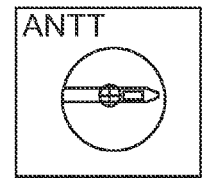
Figure 6B:
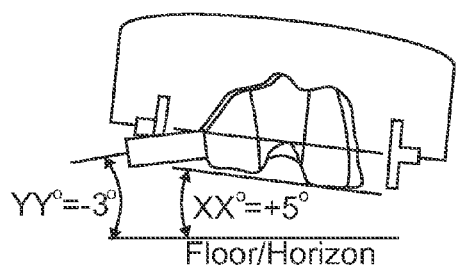
Figure 6B:
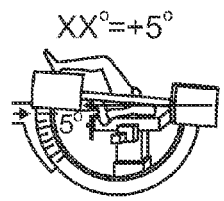
Figure 6B:
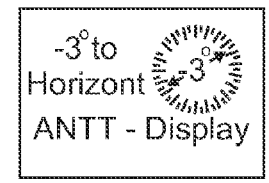
Figure 6C:
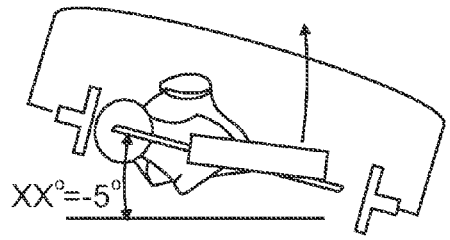
Figure 6C:
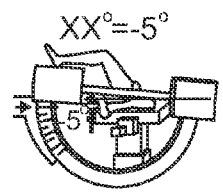
Figure 6C:
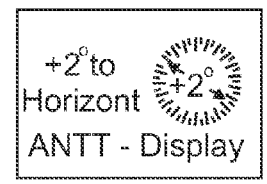

FIGS. 6a-6c illustrate a method for dealing a femur fracture with an antegrade entry of a femur nail with proximal distal locking. The distal locking will be conducted with the method described with respect to FIG. 3. Subsequently, the axis of the condyles will be determined and the difference will, be transferred to a collimator unit being fixed to the targeting device 70. Then the collimator unit will be proximal of the femur adjusted to arrive at the desired angle of the femur neck. The setting of the femur neck may be checked by an x-ray collimator unit or k-wire markers. If the rotation matches the predefined rotary orientation the proximal locking finished the procedure.

In more detail, the method for positioning a proximal femur fragment 20 and a distal femur fragment 30 with respect to each other will be described in the following. The antegrade intramedullary femur nail 40 has a proximal end 50 coupled to a targeting device 70 and a distal end 62. The antegrade intramedullary femur nail will be positioned S10 in a predefined orientation to the distal femur fragment and locking S20 of the distal end of the antegrade intramedullary femur nail to the distal femur fragment is conducted, e.g. using the method described with respect to FIG. 3, as can be seen in FIG. 6a. Afterwards a rotary orientation of the antegrade intramedullary femur nail with respect to the distal femur fragment is determined by fitting S36 the distal femur fragment to a first unique imaging projection direction 32 of an anatomical landmark of the distal femur fragment and sensing S32 the rotary orientation of a distal locking means 62 of the antegrade intramedullary femur nail with respect to the first unique imaging projection direction. For this purpose the imaging device will be adjusted until the condyles are in line, i.e. show matching contours in the imaging device 200 resulting in the first unique imaging projection direction 22, which is at the distal femur condyles. The orientation angel of the imaging device will be noticed, which is +5°, as can be seen in FIG. 6b, which is −3° visible on the ANTT display after distal locking. Then the proximal femur fragment and the distal femur fragment will be positioned S40 in a predefined rotary orientation with respect to each other by matching S50 the rotary orientation of the antegrade intramedullary femur nail with respect to the proximal femur fragment by sensing S52 the rotary orientation of a proximal locking means 52 of the antegrade intramedullary femur nail, and by fitting S56 the proximal femur fragment to a second unique imaging projection direction 22 of an anatomical landmark of the proximal femur fragment with respect to the rotary orientation of the proximal locking means, as can be seen in FIG. 6c. For this step, the imaging device will be moved to the proximal end of the femur, and be adjusted until it is in line with the femur neck, which is a −5° orientation of the imaging device. Then the targeting device 70 with the implant 40 having locked thereon the distal femur fragment 30 is rotated until +2° is visible on the ANTT display. This +2° results from −3° ANTT display, as can be seen in FIG. 6b, +5° of the distal imaging device orientation, as can be seen in FIG. 6b, −5° of the proximal imaging device orientation, as can be seen in FIG. 6c, +5° for 15° anteversion. Finally the proximal end of the antegrade intramedullary femur nail will be locked S60 to the proximal femur fragment such that the proximal femur fragment and the distal femur fragment are positioned in the predefined rotary orientation to each other. As an option the proximal end of the antegrade intramedullary femur nail may be locked to the proximal femur fragment by sensing S62 the position of the proximal locking means of the antegrade intramedullary femur nail, and positioning S63 and locking S64 the proximal femur fragment to the antegrade intramedullary femur nail.

Figure 7A:
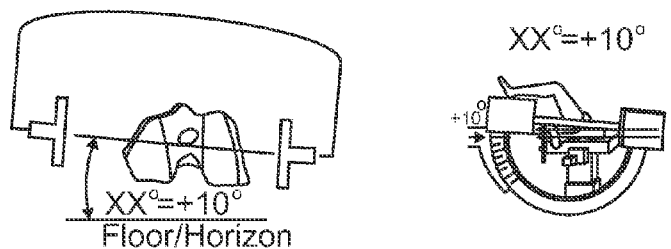
FIGS. 7a-7c illustrate a tibia fracture with retrograde entry of the intramedullary nail and primary distal locking.
Figure 7B:
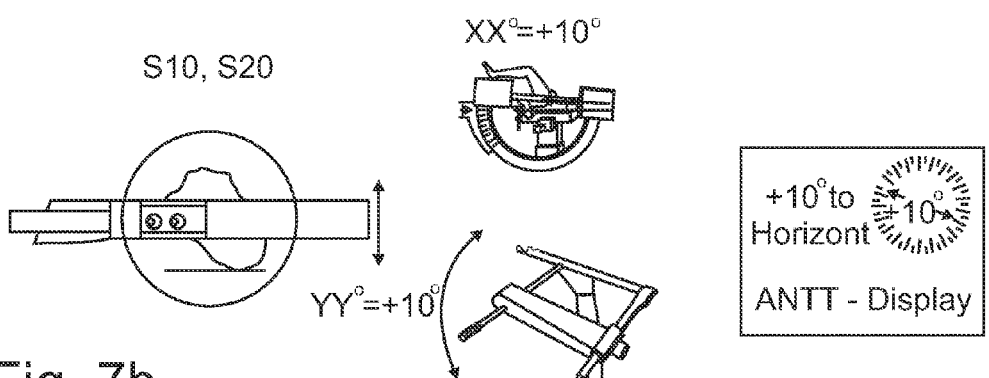
Figure 7C:
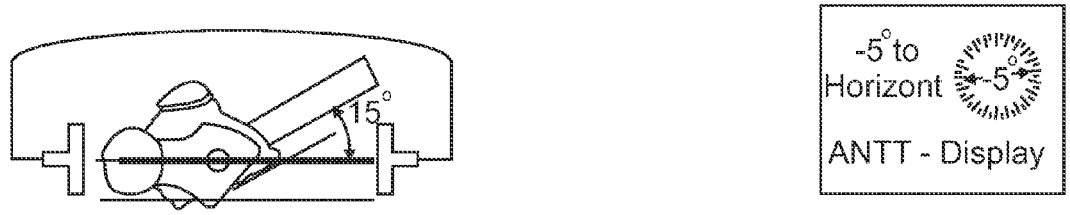

FIGS. 7a-7c illustrate a tibia fracture with retrograde entry of the intramedullary nail and primary distal locking. A retrograde insertion means to enter the bone from the distal end and to move the implant 40 from the distal end to the proximal end of the bone. Thus the direction of a retrograde insertion is rotated by 180° over the antegrade insertion. This results in the distal end 60 of the implant 40 corresponding to the proximal end 20 of the bone 10 and the proximal end 50 of the implant 40 corresponding to the distal end 30 of the bone 10. For this method, at first, the distal femur fragment will be locked to the proximal end of the implant, subsequently the rotary orientation of the nail is determined by using the ANTT method described with respect to FIG. 3, and the unique imaging projection direction of the femur condyles. This rotary orientation will be transferred to the collimation unit. The femur neck will be collimated or a k-wire marker will be set, so that subsequently the distal end of the implant can be locked to the proximal end of the femur using the ANTT described with respect to FIG. 3.

In more detail, the method for positioning a proximal femur fragment 20 and a distal femur fragment 30 with respect to each other by an retrograde intramedullary femur nail 40 having a proximal end 50 coupled to a targeting device 70 and a distal end 60 will be conducted as follows. The retrograde intramedullary femur nail will be positioned S10 in a predefined orientation to the distal femur fragment. Subsequently a rotary orientation of the retrograde intramedullary femur nail with respect to the distal femur fragment will be determined by fitting S36 the distal femur fragment to a first unique imaging projection direction 32 of an anatomical landmark of the distal femur fragment, as can be seen in FIG. 7a. For this purpose the imaging device is adjusted with the matching contours of the condyles, resulting in a +10° orientation of the imaging device in the example shown in FIG. 7a. The rotary orientation of a proximal locking means 52 of the retrograde intramedullary femur nail with respect to the first unique imaging projection direction is sensed. The latter may be conducted by the ANTT method described with respect to FIG. 3, till then targeting device 70 is in line with the orientation of the imaging device, i.e. the first unique imaging direction. Then the proximal end of the retrograde intramedullary femur nail will be locked S20 to distal femur fragment, as can be seen in FIG. 7b. Subsequently, the proximal femur fragment and the distal femur fragment are positioned in a predefined rotary orientation with respect to each other by matching S50 the rotary orientation of the retrograde intramedullary femur nail with respect to the proximal femur fragment. For this purpose, the imaging device is moved to the proximal femur end and adjusted to be in line with the femoral neck as the second unique imaging projection direction. In the example shown in FIG. 7c, the imaging device orientation is parallel to the floor (i.e. 0° over the floor). As an option the rotary orientation of a distal locking means 62 of the retrograde intramedullary femur nail can be sensed and the proximal femur fragment can be fitted S56 to the second unique imaging projection direction 22 of an anatomical landmark, i.e. the head of the proximal femur fragment with respect to the rotary orientation of the distal locking means. The targeting device 70 with the condyles fragment will be rotated until −5° is visible on the ANTT display. This results from the orientation of the imaging device of 0° in FIG. 7c, +10° orientation of the condyles in FIG. 7a and the required anteversion of assumed 15°. Finally the distal end of the retrograde intramedullary femur nail is locked to the proximal femur fragment such that the proximal femur fragment and the distal femur fragment are positioned in the predefined rotary orientation to each other. The locking can optionally be supported by the method as described with respect to FIG. 3, wherein locking the distal end of the retrograde intramedullary femur nail to the proximal femur fragment is conducted by sensing S62 the position of the distal locking means of the retrograde intramedullary femur nail, and positioning S63 and locking S64 the proximal femur fragment to the retrograde intramedullary femur nail.

Figure 8A:
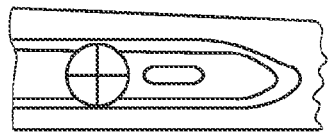
FIGS. 8a-8c illustrate a method for dealing a tibia fracture with antegrade entry of the intramedullary tibia nail with primary distal locking.
Figure 8A:
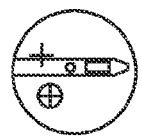
Figure 8A:
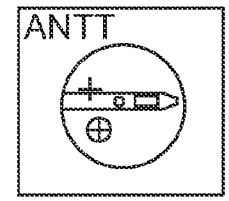
Figure 8A:
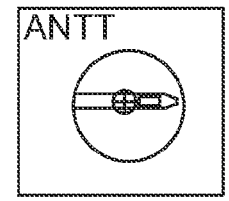
Figure 8B:
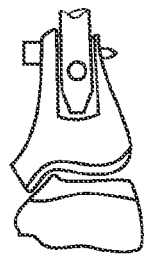
Figure 8B:
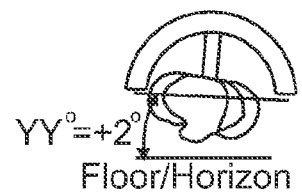
Figure 8B:
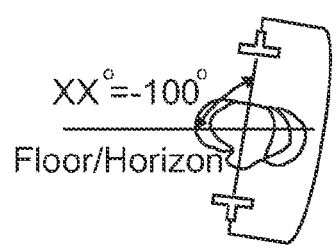
Figure 8B:
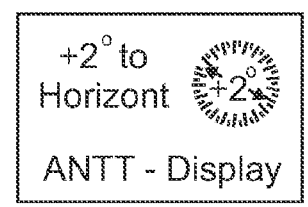
Figure 8C:
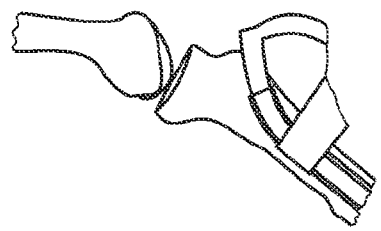
Figure 8C:
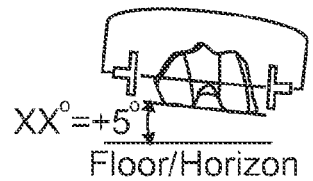
Figure 8C:
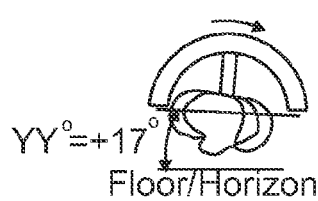
Figure 8C:
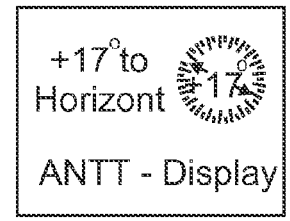

FIGS. 8a-8c illustrate a method for dealing a tibia fracture with antegrade entry of the intramedullary tibia nail with primary distal locking. This method starts with a distal locking of the as described with respect to FIG. 3, as can be seen in FIG. 8a. The imaging device will be AP adjusted to the sub-talar joint. The rotation of the tibia nail will be determined and the collimating unit is proximally set and adjusted at the targeting device, and subsequently re-adjusted with a 20° to 25° rotation outwardly. The orientation of the imaging device is checked with respect to the unique imaging projection direction of the condyles of the femur at the full extended knee.

In more detail, the method for positioning a proximal tibia fragment 20 and a distal tibia fragment 20 with respect to each other by an antegrade intramedullary tibia nail 40 having a proximal end 50 coupled to a targeting device 70 and a distal end 60 is conducted as follows. The antegrade intramedullary tibia nail is positioned S10 in a predefined orientation to the distal tibia fragment and the distal end of the antegrade intramedullary tibia nail is locked S20 to the distal tibia fragment. The ANTT method described with respect to FIG. 3 may be used, as can be seen in FIG. 8a. Then a rotary orientation of the antegrade intramedullary tibia nail with respect to the distal tibia fragment will be determined by fitting the distal tibia fragment to a first unique imaging projection direction 32 of an anatomical landmark, here the talar joint of the distal tibia fragment and sensing S32 the rotary orientation of a distal locking means 62 of the antegrade intramedullary tibia nail with respect to the first unique imaging projection direction. In this example the imaging device is adjusted to arrive at the unique imaging projection direction of the talar joint. The orientation of the imaging device in this example is −100° (90°+10°), wherein +2° are visible on the ANTT display after distal locking, as can be seen in FIG. 8b. Subsequently the proximal tibia fragment and the distal tibia fragment are positioned S40 in a predefined rotary orientation with respect to each other by matching S50 the rotary orientation of the antegrade intramedullary tibia nail with respect to the proximal tibia fragment by sensing S52 the rotary orientation of a proximal locking means 52 of the antegrade intramedullary tibia nail, and by fitting S56 the proximal tibia fragment to a second unique imaging projection direction 22 of an anatomical landmark of the proximal tibia fragment, here the condyles with respect to the rotary orientation of the proximal locking means. For this purpose, the imaging device will be adjusted till in line with the unique imaging projection direction of the condyles, here +5°, as can be seen in FIG. 8c. The targeting device with the tibia nail having locked thereon the distal tibia fragment is rotated to arrive at the rotary orientation of +17° resulting from +2° from ANTT display as can be seen in FIG. 8b, +15°+15° result from the +5° of the condyles inclination as can be seen in FIG. 8c and the (90°)+10° from the talar inclination, as can be seen in FIG. 8b to arrive at the required 20° outward rotation. Finally the proximal end of the antegrade intramedullary tibia nail is locked S60 to the proximal tibia fragment such that the proximal tibia fragment and the distal tibia fragment are positioned in the predefined rotary orientation to each other. Optionally, the locking can be conducted as outlined with respect to FIG. 3, wherein locking the proximal end of the antegrade intramedullary tibia nail to the proximal tibia fragment is conducted by sensing S62 the position of the proximal locking means of the antegrade intramedullary tibia nail, and positioning S63 and locking S64 the proximal tibia fragment to the antegrade intramedullary tibia nail.

FIGS. 9a-9d illustrate a tibia fracture with an antegrade entry of the intramedullary tibia nail with primary proximal locking. The proximal locking will be conducted via the targeting device. The condyle plane is determined in the full extended knee, and the collimation unit is adjusted to the frontal plane. Subsequently, the outward rotation for the talar joint is adjusted and the tibia is rotated to be locked in the correct position.

Figure 9A:
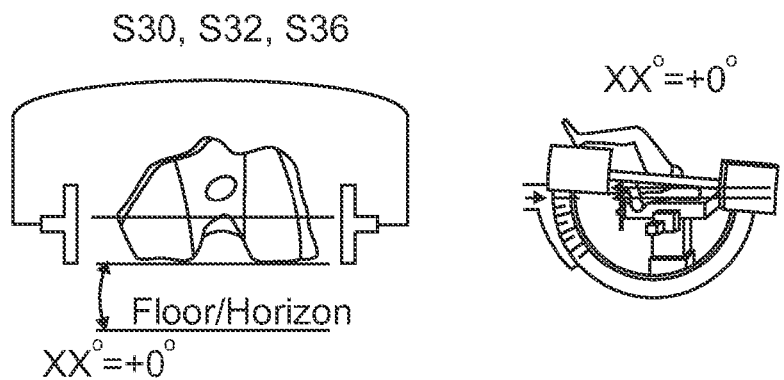
FIGS. 9a-9d illustrate a tibia fracture with an antegrade entry of the intramedullary tibia nail with primary proximal locking.
Figure 9B:
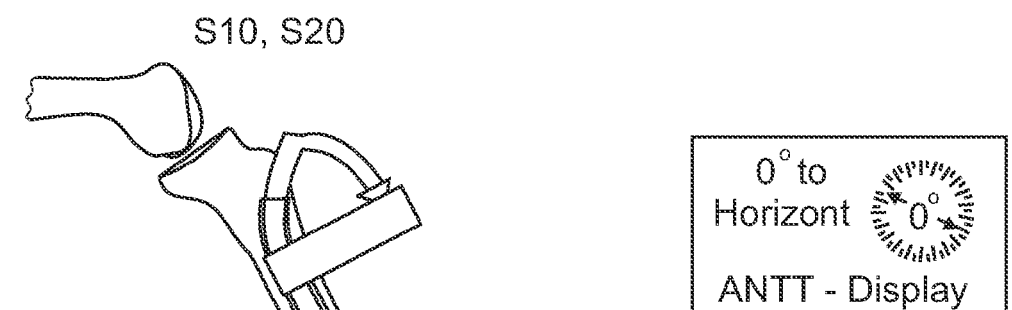
Figure 9C:
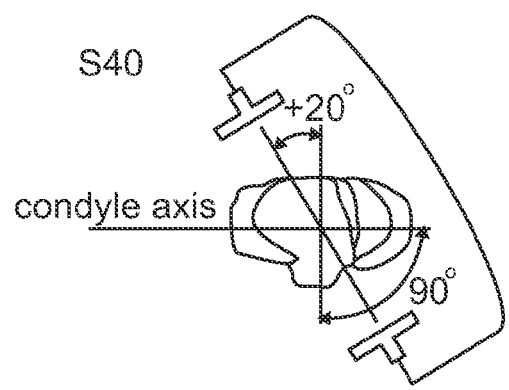
Figure 9D:
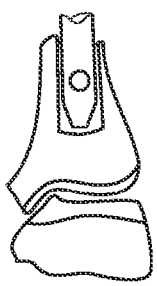

In more detail the method for positioning a proximal tibia fragment 20 and a distal tibia fragment 30 with respect to each other by an antegrade intramedullary tibia nail 40 having a proximal end 60 coupled to a targeting device 70 and a distal end 50 will be conducted as follows. A rotary orientation of the antegrade intramedullary tibia nail with respect to the proximal tibia fragment is determined by fitting S36 the proximal tibia fragment to a first unique imaging projection direction 22 of an anatomical landmark of the proximal tibia fragment, as can be seen in FIG. 9a. The imaging device is adjusted to be in line with the unique imaging projection direction of the condyles, i.e. the anatomical landmark of the proximal tibia fragment. In this example, the orientation of the imaging device is 0°. The antegrade intramedullary tibia nail is positioned S10 in a predefined orientation to the proximal tibia fragment and the rotary orientation of a proximal locking means 52 of the antegrade intramedullary tibia nail is sensed S32 with respect to the first unique imaging projection direction. In this example, the targeting device 70 as a representation of the tibia nail is brought in line with unique condyle projection of FIG. 9a, as can be seen in FIG. 9b. Then the proximal end of the antegrade intramedullary tibia nail is locked S20 to proximal tibia fragment. Then the imaging device is moved to the distal tibia end, as can be seen in FIG. 9c, and moved by 90° to arrive in the correct reference plane and then 20° to 23° are added to obtain the predefined rotary orientation of the distal tibia fragment and the proximal tibia fragment to each other, as can be seen in FIG. 9c. The proximal tibia fragment and the distal tibia fragment are positioned in a predefined rotary orientation with respect to each other by matching S50 the rotary orientation of the antegrade intramedullary tibia nail with respect to the distal tibia fragment by sensing S52 the rotary orientation of a distal locking means 62 of the antegrade intramedullary tibia nail via the targeting device, and by fitting S56 the distal tibia fragment to a second unique imaging projection direction 32 of an anatomical landmark of the distal tibia fragment with respect to the rotary orientation of the distal locking means. The latter will be obtained by rotated the distal fragment until the sub-talar joint is fully visible, i.e. the anatomical landmark of the talar joint corresponds to the preset orientation of the imaging device, i.e. the unique imaging projection direction of the distal end of the tibia, as can be seen in FIG. 9d. Finally the distal end of the antegrade intramedullary tibia nail is locked S60 to the distal tibia fragment such that the proximal tibia fragment and the distal tibia fragment are positioned in the predefined rotary orientation to each other. As an option, locking can be conducted by the ANTT, as described with respect to FIG. 3, wherein locking the distal end of the antegrade intramedullary tibia nail to the distal tibia fragment is conducted by sensing S62 the position of the distal locking means of the antegrade intramedullary tibia nail, and positioning S63 and locking S64 the distal tibia fragment to the antegrade intramedullary tibia nail.

Figure 10:
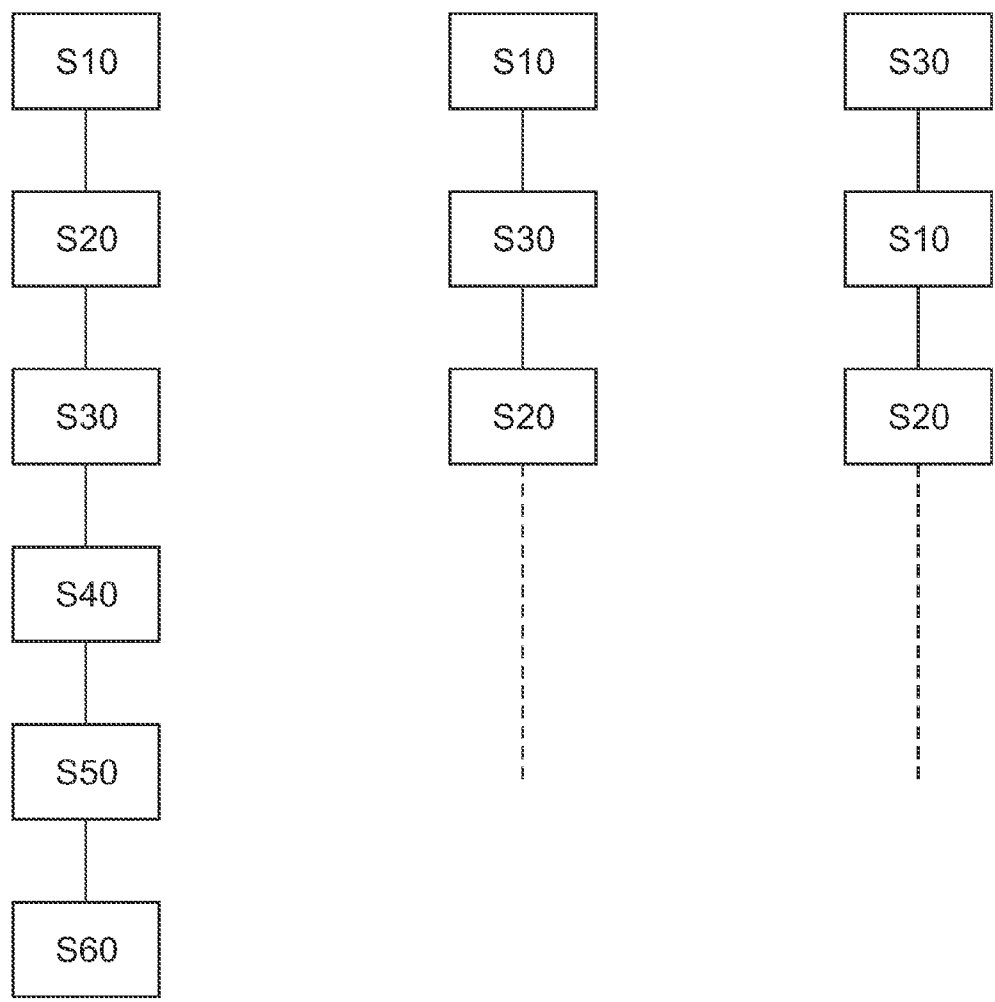
FIG. 10 illustrates procedural steps and alternatives thereto for a method for dealing a re-establishment of the orientation of extremity bone fragments according to an exemplary embodiment of the invention.

FIG. 10 illustrates procedural steps and alternatives thereto for a generalized method for dealing a re-establishment of the orientation of extremity bone fragments according to an exemplary embodiment of the invention. The method for positioning a first intramedullary bone fragment 20 and a second intramedullary bone fragment 30 of a fractured extremity bone 10 to be restored with respect to each other by an intramedullary implant 40 having a proximal end 50 coupled to a targeting device 70 and a distal end 60 can generally be expressed by the following steps which should cover all of the five above described methods. The generalized method comprises positioning S10 of the intramedullary implant in a predefined rotary orientation to the first intramedullary bone fragment, locking S20 one of the proximal end and the distal end of the intramedullary implant to the first intramedullary bone fragment, determining S30 a rotary orientation of the intramedullary implant with respect to the first intramedullary bone fragment, positioning S40 of the first intramedullary bone fragment and the second intramedullary bone fragment in a predefined rotary orientation with respect to each other by matching S50 the rotary orientation of the intramedullary implant with respect to the second intramedullary bone fragment, locking S60 the other of the proximal end and the distal end of the intramedullary implant to the second intramedullary bone fragment, wherein locking the distal end of the intramedullary implant to the respective intramedullary bone fragment is conducted by sensing S22, S62 the actual position of a distal locking means 62 of the intramedullary implant, and positioning S28, S68 and locking S29, S69 the respective intramedullary bone fragment to the intramedullary implant such that the intramedullary implant allows a positioning of the first intramedullary bone fragment and the second intramedullary bone fragment in the predefined rotary orientation to each other.

As can be seen from FIG. 10, the order of the steps is not fixed and may differ. This can also be taken from the detained description of the five above described methods, in which the order of the steps S10, S20 and S30 may differ according to required order.

The method may optionally use unique imaging projection direction of anatomical landmarks, such that determining S30 a rotary orientation of the intramedullary implant 40 with respect to the first intramedullary bone fragment 20 may comprise fitting S36 the first intramedullary bone fragment to a first unique imaging projection direction 22 of an anatomical landmark of the first intramedullary bone fragment, and matching S50 the rotary orientation of the intramedullary implant with respect to the second intramedullary bone fragment 30 comprises fitting S56 the second intramedullary bone fragment to a second unique imaging projection direction 32 of an anatomical landmark of the second intramedullary bone fragment, wherein the rotary orientation of the first unique projection and the second unique projection to each other corresponds to the predefined rotary orientation of the first intramedullary bone fragment and the second intramedullary bone fragment to each other. Further, sensing S22, S62 the actual position of a distal locking means 62 of the intramedullary implant 40 may comprise using an actual position of a proximal locking means 52 of the intramedullary implant, and the orientation of the first unique projection 22 and the second unique projection 32 are used to provide the surgeon with positional information for the first intramedullary bone fragment 20 with respect to the second intramedullary bone fragment 30.

Furthermore, sensing S22, S62 the actual position of a distal locking means 62 of the intramedullary implant 40 may be conducted by transmitting S23, S63 a signal from an external transmitting unit 72, receiving S24, S64 the signal by an internal transceiving unit 64 being fixedly mounted relative to the distal locking means 62 of the intramedullary implant 40 and being actuated by the external transmitting unit, transmitting S25, S65 by acoustic vibrations or acoustic waves the received signal, as indicative of the relative position of the transceiving unit with respect to the external transmitting unit, to an external receiving unit 74, as it is described with respect to FIG. 3 in more detail. This method is also referred to as ANTT method, which means an active nail tip targeting. The transceiving unit 64 may be provided as an active unit capable of calculating the relative position of the nail tip and of transmitting this information to the targeting device so as to simplify the determination of the position of the locking holes in the nail implant. With this respect, the locking direction of an end 50, 60 of the intramedullary implant 40 may correspond to the respective unique imaging projection direction 22, 32 of the respective intramedullary bone fragment 20, 30 to be locked to that respective end of the intramedullary implant.

It should be noted that the general inventive principle may also be applied to other fractures with fragments having an anatomical landmark.

It should be noted that the term 'comprising' does not exclude other elements or steps and the 'a' or 'an' does not exclude a plurality. Also elements described in association with the different embodiments may be combined.

It should be noted that the reference signs in the claims shall not be construed as limiting the scope of the claims.

The invention claimed is:

1. A method for operating a device for restoring the position of a first intramedullary bone fragment and a second intramedullary bone fragment of a fractured extremity bone with respect to each other by an intramedullary implant having a proximal end and a distal end, the proximal end coupled to a targeting device, the method comprising:

determining the orientation of the first intramedullary bone fragment by fitting a first unique imaging projection direction of an anatomical landmark of the first intramedullary bone fragment to the first intramedullary bone fragment;

determining a future position of the intramedullary implant in a predefined orientation to the first intramedullary bone fragment;

determining a locking position of one of the proximal end and the distal end of the intramedullary implant to the first intramedullary bone fragment;

determining a future position of the first intramedullary bone fragment and the second intramedullary bone fragment in a predefined rotary orientation with respect to each other by determining a second unique imaging projection direction of an anatomical landmark of the second intramedullary bone fragment, wherein the orientation of the first unique imaging projection direction and the second unique imaging projection direction to each other corresponds to the predefined rotary orientation of the first intramedullary bone fragment and the second intramedullary bone fragment to each other;

determining a locking position of the other of the proximal end and the distal end of the intramedullary implant to the second intramedullary bone fragment; and wherein determining a locking position of the distal end of the intramedullary implant to the respective intramedullary bone fragment is conducted by sensing the actual position of a distal locking means of the intramedullary implant, and determining a locking position of the respective intramedullary bone fragment to the intramedullary implant such that the intramedullary implant allows a positioning of the first intramedullary bone fragment and the second intramedullary bone fragment in the predefined rotary orientation to each other, wherein sensing the actual position of a distal locking means of the intramedullary implant is conducted by transmitting a signal from an external transmitting unit being positioned in a predefined position; receiving the signal by an internal transceiving unit being fixedly mounted relative to the distal locking means of the intramedullary implant and being actuated by the external transmitting unit; and transmitting a signal to an external receiving unit by acoustic vibrations or acoustic waves as indicative of the relative position of the internal transceiving unit with respect to the external transmitting unit.

2. The method of claim 1, wherein sensing the actual position of a distal locking means of the intramedullary implant comprises using an actual position of a proximal locking means of the intramedullary implant, and the orientation of the first unique imaging projection direction and the second unique imaging projection direction are used for providing the surgeon with positional information for the first intramedullary bone fragment and the second intramedullary bone fragment.

3. The method of claim 1, wherein providing the surgeon with positional information comprises providing displacement information, based on which the surgeon can bring the first intramedullary bone fragment and the second intramedullary bone fragment in the predetermined rotary orientation to each other.

4. A method for operating a device for restoring the position of a first bone fragment and a second bone fragment of a fractured extremity bone with respect to each other by an intramedullary implant having a proximal end and a distal end, the proximal end coupled to a targeting device, the method comprising:

determining the orientation of the first bone fragment by fitting a first unique imaging projection direction of an anatomical landmark of the first bone fragment to the first bone fragment;

determining a future position of the intramedullary implant in a predefined orientation to the first intramedullary bone fragment;

determining a locking position of one of the proximal end and the distal end of the intramedullary implant to the first bone fragment;

determining a future position of the first bone fragment and the second bone fragment in a predefined rotary orientation with respect to each other by determining a second unique imaging projection direction of an anatomical landmark of the second bone fragment, wherein the orientation of the first unique imaging projection direction and the second unique imaging projection direction to each other corresponds to the predefined rotary orientation of the first bone fragment and the second bone fragment to each other;

determining a locking position of the other of the proximal end and the distal end of the intramedullary implant to the second bone fragment; and wherein determining a locking position of the distal end of the intramedullary implant to the respective bone fragments is conducted by sensing the actual position of a distal locking means of the intramedullary implant, and determining a locking position of the respective bone fragment to the intramedullary implant such that the intramedullary implant allows a positioning of the first bone fragment and the second bone fragment in the predefined rotary orientation to each other; and wherein the anatomical landmark of the first bone fragment is a femoral head and the anatomical landmark of the second bone fragment is the femoral condyles, wherein sensing the actual position of a distal locking means of the intramedullary implant is conducted by transmitting a signal from an external transmitting unit being positioned in a predefined position; receiving the signal by an internal transceiving unit being fixedly mounted relative to the distal locking means of the intramedullary implant and being actuated by the external transmitting unit; and transmitting a signal to an external receiving unit by acoustic vibrations or acoustic waves as indicative of the relative position of the internal transceiving unit with respect to the external transmitting unit.

5. The method of claim 4, wherein sensing the actual position of a distal locking means of the intramedullary implant comprises using an actual position of a proximal locking means of the intramedullary implant, and the orientation of the first unique imaging projection direction and the second unique imaging projection direction are used for providing the surgeon with positional information for the first bone fragment and the second bone fragment.

6. The method of claim 4, wherein providing the surgeon with positional information comprises providing displacement information, based on which the surgeon can bring the first intramedullary bone fragment and the second intramedullary bone fragment in the predetermined rotary orientation to each other.

7. A method for operating a device for restoring the position of a first intramedullary bone fragment and a second intramedullary bone fragment of a fractured extremity bone with respect to each other by an intramedullary implant having a proximal end and a distal end, the proximal end coupled to a targeting device, the method comprising:

determining the orientation of the first intramedullary bone fragment by fitting a first imaging projection direction of an anatomical landmark of the first intramedullary bone fragment to the first intramedullary bone fragment, the imaging projection direction shows a characteristic of the anatomical landmark which allows determination of a clearly defined orientation;

determining a future position of the intramedullary implant in a predefined orientation to the first intramedullary bone fragment;

determining a locking position of one of the proximal end and the distal end of the intramedullary implant to the first intramedullary bone fragment;

determining a future position of the first intramedullary bone fragment and the second intramedullary bone fragment in a predefined rotary orientation with respect to each other by determining a second unique imaging projection direction of an anatomical landmark of the second intramedullary bone fragment, wherein the orientation of the first unique imaging projection direction and the second imaging projection direction to each other corresponds to the predefined rotary orientation of the first intramedullary bone fragment and the second intramedullary bone fragment to each other;

determining a locking position of the other of the proximal end and the distal end of the intramedullary implant to the second intramedullary bone fragment; and wherein determining a locking position of the distal end of the intramedullary implant to the respective intramedullary bone fragment is conducted by sensing the actual position of a distal locking means of the intramedullary implant, and determining a locking position of the respective intramedullary bone fragment to the intramedullary implant such that the intramedullary implant allows a positioning and locking of the first intramedullary bone fragment and the second intramedullary bone fragment in the predefined rotary orientation to each other, wherein sensing the actual position of a distal locking means of the intramedullary implant is conducted by transmitting a signal from an external transmitting unit being positioned in a predefined position; receiving the signal by an internal transceiving unit being fixedly mounted relative to the distal locking means of the intramedullary implant and being actuated by the external transmitting unit; and transmitting a signal to an external receiving unit by acoustic vibrations or acoustic waves as indicative of the relative position of the internal transceiving unit with respect to the external transmitting unit.

8. The method of claim 7, wherein sensing the actual position of a distal locking means of the intramedullary implant comprises using an actual position of a proximal locking means of the intramedullary implant, and the orientation of the first unique imaging projection direction and the second unique imaging projection direction are used for providing the surgeon with positional information for the first intramedullary bone fragment and the second intramedullary bone fragment.

9. The method of claim 7, wherein providing the surgeon with positional information comprises providing displacement information, based on which the surgeon can bring the first intramedullary bone fragment and the second intramedullary bone fragment in the predetermined rotary orientation to each other.

* * * * *